United States Patent
Kaur et al.

(10) Patent No.: US 11,597,962 B2
(45) Date of Patent: Mar. 7, 2023

(54) RAPID SELECTIVE DETECTION OF BACTERIA

(71) Applicant: Chapman University, Orange, CA (US)

(72) Inventors: Kamaljit Kaur, Irvine, CA (US); Hanieh Hossein-Nejad-Ariani, Irvine, CA (US)

(73) Assignee: Chapman University, Orange, CA (US)

( * ) Notice: Subject to any disclaimer, the term of this patent is extended or adjusted under 35 U.S.C. 154(b) by 250 days.

(21) Appl. No.: 16/763,902

(22) PCT Filed: Nov. 14, 2018

(86) PCT No.: PCT/US2018/060956
§ 371 (c)(1),
(2) Date: May 13, 2020

(87) PCT Pub. No.: WO2019/099467
PCT Pub. Date: May 23, 2019

(65) Prior Publication Data
US 2020/0347431 A1    Nov. 5, 2020

Related U.S. Application Data

(60) Provisional application No. 62/585,883, filed on Nov. 14, 2017.

(51) Int. Cl.
*C12Q 1/06* (2006.01)
*G01N 33/569* (2006.01)

(52) U.S. Cl.
CPC ............ *C12Q 1/06* (2013.01); *G01N 33/569* (2013.01); *G01N 33/56911* (2013.01); *G01N 2333/195* (2013.01); *G01N 2333/255* (2013.01)

(58) Field of Classification Search
CPC ............... C12Q 1/06; G01N 33/569; G01N 33/56911; G01N 2333/195; G01N 2333/255; G01N 33/56916
See application file for complete search history.

(56) References Cited

PUBLICATIONS

Azmi et al. "Detection of Listeria monocytogenes with short peptide fragments from class IIa bacteriocins as recognition elements, "ACS Comb Sci,Jan. 20, 2015 (Jan. 20, 2015),vol. 17, No. 3,pp. 156-163. entire document (Year: 2015).*
Etayash et al., (ACS Applied Materials and Interfaces 2014, 6, pp. 11131-31118; Published Dec. 20, 2013). (Year: 2013).*
Azmi et al. "Detection of Listeria monocytogenes with short peptide fragments from class IIa bacteriocins as recognition elements," ACS Comb Sci, Jan. 20, 2015 (Jan. 20, 2015), vol. 17, No. 3, pp. 156-163. (Year: 2015).*
Guralp et al., (Biochemical Engineering Journal vol. 101, Sep. 15, 2015, pp. 18-22). (Year: 2015).*

\* cited by examiner

*Primary Examiner* — Jana A Hines
(74) *Attorney, Agent, or Firm* — K&L Gates LLP; Louis C. Cullman; Michelle Glasky Bergman

(57) ABSTRACT

A rapid assay for determining the presence of bacteria in a sample, such as a contaminated food sample, is disclosed. The assay comprises contacting the sample with a bacteria-specific ligand associated with a substrate, wherein bacteria present in the sample bind the ligand; contacting the bound bacteria with a detection agent; detecting the presence of bacteria in the sample by measuring the quantity of detection agent associated with the sample.

10 Claims, 14 Drawing Sheets
Specification includes a Sequence Listing.

Leucocin A    KYYGNGVHCTKSGCSVNWGEAFSAGVHRLANGGNGFW
Control peptide    NGVHATKSGASVNWGEAFSA

SEQUENCE LISTING

<160> NUMBER OF SEQ ID NOS: 4

<210> SEQ ID NO 1
<211> LENGTH: 37
<212> TYPE: PRT
<213> ORGANISM: Artificial Sequence
<220> FEATURE:
<223> OTHER INFORMATION: 37 amino acid Leucocin A

<400> SEQUENCE: 1

Lys Tyr Tyr Gly Asn Gly Val His Cys Thr Lys Ser Gly Cys Ser Val
1               5                   10                  15

Asn Trp Gly Glu Ala Phe Ser Ala Gly Val His Arg Leu Ala Asn Gly
            20                  25                  30

Gly Asn Gly Phe Trp
        35

<210> SEQ ID NO 2
<211> LENGTH: 20
<212> TYPE: PRT
<213> ORGANISM: Artificial Sequence
<220> FEATURE:
<223> OTHER INFORMATION: Control Leucocin A fragment

<400> SEQUENCE: 2

Asn Gly Val His Ala Thr Lys Ser Gly Ala Ser Val Asn Trp Gly Glu
1               5                   10                  15

Ala Phe Ser Ala
            20

<210> SEQ ID NO 3
<211> LENGTH: 74
<212> TYPE: PRT
<213> ORGANISM: Escherichia coli

<400> SEQUENCE: 3

Gly Asp Pro Leu Ala Asp Pro Asn Ser Gln Ile Val Arg Gln Ile Met
1               5                   10                  15

Ser Asn Ala Ala Trp Gly Ala Ala Phe Gly Ala Arg Gly Gly Leu Gly
            20                  25                  30

Gly Met Ala Val Gly Ala Ala Gly Gly Val Thr Gln Thr Val Leu Gln
        35                  40                  45

Gly Ala Ala Ala His Met Pro Val Asn Val Pro Ile Pro Lys Val Pro
    50                  55                  60

Met Gly Pro Ser Trp Asn Gly Ser Lys Gly
65                  70

<210> SEQ ID NO 4
<211> LENGTH: 11
<212> TYPE: PRT
<213> ORGANISM: Artificial Sequence
<220> FEATURE:
<223> OTHER INFORMATION: Control peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (8)..(8)
<223> OTHER INFORMATION: X = D-lysine

```
<400> SEQUENCE: 4

Trp Xaa Glu Ala Ala Tyr Gln Xaa Phe Leu Ala
1               5                   10
```

RAPID SELECTIVE DETECTION OF BACTERIA

CROSS-REFERENCE TO RELATED APPLICATIONS

The present application is a US National phase application of International Application PCT/US2018/060956 filed Nov. 14, 2018, which claims the benefit of U.S. Provisional patent application 62/585,883 filed Nov. 14, 2017, the entire contents of which are incorporated by reference herein.

FIELD

The present disclosure is drawn to rapid assays for the detection of bacteria in samples.

BACKGROUND

*Listeria monocytogenes*, a Gram-positive non-spore-forming rod bacterium, is the cause for foodborne illnesses including listeriosis, and has a high mortality rate of 20-40%. The bacteria can grow at 4° C. posing safety concerns for ready-to-eat products, such as cheese, meat, vegetables, and pharmaceuticals. Rapid and specific detection methods for *L. monocytogenes* can help diminish some of the dangers associated with this pathogen.

Conventionally there are two general methods to detect foodborne pathogens. One is a nucleic acid-based method which involves polymerase chain reaction (PCR) techniques. This method enables high-throughput analysis, but has some shortcomings including that it is time consuming and yields false-positive results. The second method is immunologically-based, which utilizes antibodies for selective detection of pathogens. This technique is specific, sensitive, and precise but the use of antibodies makes it comparatively expensive.

A more recent strategy uses biosensor-based methods, which may use some components of the two above-mentioned techniques. The general characteristics of any biosensor include being time-efficient, compact, portable, sensitive, and not labor-intensive. A biosensor utilizes a molecular recognition motif, such as an antibody, a carbohydrate, an aptamer, a peptide, or mixture of these ligands, that bind bacteria specifically. The binding is read, to detect bacteria, using different transduction methods that can be categorized into optical, mechanical, electrochemical, potentiometric, or impedimetric biosensors.

The biosensor approach has been explored for specific detection of *L. monocytogenes*. Most of the proposed biosensors use antibodies against *L. monocytogenes*, and include approaches such as an immunochromatography strip test that specifically detects *L. monocytogenes*, or a multiplex fiber optic biosensor for simultaneous detection of three food borne pathogens, *L. monocytogenes*, *E. coli* O157:H7 and *S. enterica*. Also previously used is a *Listeria*-specific antimicrobial peptide, Leucocin A, for specific binding and detection of *L. monocytogenes* using microcantilever, impedance spectroscopy, and fluorescence microcopy techniques.

SUMMARY

Disclosed herein are assays for determining the presence of *Listeria* bacteria in a sample comprising: contacting the sample with a bacteria-specific ligand associated with a substrate, wherein *Listeria* bacteria present in the sample bind the ligand, wherein the bacteria-specific ligand is Leucocin A; contacting the bound *Listeria* bacteria with a detection agent; and detecting the presence of *Listeria* bacteria in the sample by measuring the quantity of detection agent associated with the sample.

In some embodiments of the *Listeria* assay, the substrate is a glass surface. In some embodiments of the *Listeria* assay, the substrate is a porous membrane. In some embodiments of the *Listeria* assay, the membrane is a PDVF membrane. In some embodiments of the *Listeria* assay, the bacteria-specific ligand associated with a substrate comprises LeuA spots immobilized on a glass substrate. In some embodiments of the *Listeria* assay, the bacteria-specific ligand associated with a substrate comprises LeuA spots immobilized on a PVDF membrane.

In some embodiments of the *Listeria* assay, the sample is a food sample. In some embodiments of the *Listeria* assay, the food sample is a milk sample.

In some embodiments of the *Listeria* assay, the bacteria is *Listeria* monocytogenes. In some embodiments of the *Listeria* assay, the detection agent is a gold nanocluster. In some embodiments of the *Listeria* assay, the detection comprises fluorescence detection. In some embodiments of the *Listeria* assay, if the fluorescent intensity of the detection agent for the sample is greater than the fluorescent intensity of a control, there are bacteria present in the sample. In some embodiments of the *Listeria* assay, the assay is completed in about 45-60 minutes.

Also disclosed herein are assays for determining the presence of *Salmonella* bacteria in a sample comprising: contacting the sample with a bacteria-specific ligand associated with a substrate, wherein *Salmonella* bacteria present in the sample bind the ligand, wherein the bacteria-specific ligand is microcin N; contacting the bound *Salmonella* bacteria with a detection agent; and detecting the presence of *Salmonella* bacteria in the sample by measuring the quantity of detection agent associated with the sample.

In some embodiments of the *Salmonella* assay, the substrate is a glass surface. In some embodiments of the *Listeria* assay, the substrate is a porous membrane. In some embodiments of the *Salmonella* assay, the membrane is a PDVF membrane. In some embodiments of the *Salmonella* assay, the bacteria-specific ligand associated with a substrate comprises microcin N spots immobilized on a glass substrate. In some embodiments of the *Salmonella* assay, the bacteria-specific ligand associated with a substrate comprises microcin N spots immobilized on a PVDF membrane.

In some embodiments of the *Salmonella* assay, the sample is a food sample.

In some embodiments of the *Salmonella* assay, the detection agent is a gold nanocluster. In some embodiments of the *Salmonella* assay, the detection comprises fluorescence detection. In some embodiments of the *Salmonella* assay, if the fluorescent intensity of the detection agent for the sample is greater than the fluorescent intensity of a control, there are bacteria present in the sample. In some embodiments of the *Salmonella* assay, the assay is completed in about 45-60 minutes.

Also disclosed herein are kits for detecting a *Listeria* species in a sample, the kit comprising: a *Listeria*-specific ligand associated with a substrate, wherein *Listeria*-specific ligand is Leucocin A; gold nanoclusters or reagents to prepare gold nanoclusters; and instructions for detecting a *Listeria* species in the sample using the *Listeria*-specific ligand associated with the substrate.

In some embodiments of the *Listeria* kit, the substrate is a glass surface. In some embodiments of the *Listeria* kit, the substrate is a porous membrane. In some embodiments of the *Listeria* kit, the membrane is a PDVF membrane. In some embodiments of the *Listeria* kit, the *Listeria*-specific ligand associated with a substrate comprises LeuA spots immobilized on a glass substrate. In some embodiments of the *Listeria* kit, the *Listeria*-specific ligand associated with a substrate comprises LeuA spots immobilized on a PVDF membrane.

In some embodiments of the *Listeria* kit, the *Listeria* species is *Listeria* monocytogenes. In some embodiments of the *Listeria* kit, the sample is a food sample. In some embodiments of the *Listeria* kit, the food sample is a milk sample.

In some embodiments of the *Listeria* kit, the detection comprises fluorescence detection. In some embodiments of the *Listeria* kit, if the fluorescent intensity of the detection agent for the sample is greater than the fluorescent intensity of a control, there is *Listeria* present in the sample.

Also disclosed herein are kits for detecting a *Salmonella* species in a sample, the kit comprising: a *Salmonella*-specific ligand associated with a substrate, wherein the bacteria-specific ligand is monocin N; gold nanoclusters or reagents to prepare gold nanoclusters; and instructions for detecting a *Salmonella* species in the sample using the *Salmonella*-specific ligand associated with the substrate.

In some embodiments of the *Salmonella* kit, the substrate is a glass surface. In some embodiments of the *Salmonella* kit, the substrate is a porous membrane. In some embodiments of the *Salmonella* kit, the membrane is a PDVF membrane. In some embodiments of the *Salmonella* kit, the *Salmonella*-specific ligand associated with a substrate comprises monocin N spots immobilized on a glass substrate. In some embodiments of the *Salmonella* kit, the *Salmonella*-specific ligand associated with a substrate comprises monocin N spots immobilized on a PVDF membrane.

In some embodiments of the *Salmonella* kit, the sample is a food sample.

In some embodiments of the *Salmonella* kit, the detection comprises fluorescence detection. In some embodiments of the *Salmonella* kit, if the fluorescent intensity of the detection agent for the sample is greater than the fluorescent intensity of a control, there is *Salmonella* present in the sample.

BRIEF DESCRIPTION OF THE DRAWINGS

FIG. 2A depicts UV-visible absorption and fluorescence spectra of AuNC. FIG. 2B depicts MALDI-TOF mass spectrum for MPA-AuNC using Autoflex Speed MALDI-TOF mass spectrometer in reflector positive mode, without any matrix. The mass spectrum repeatedly showed peaks at 1230.5 Da and 1246.4 Da which corresponds to 4 Au and 4 MPA (calcd. $[M+Na]^{+1}$ 1230.2 and $[M+K]^{+1}$ 1246.2, respectively).

FIGS. 8A and 8C depict MALDI-TOF mass spectra for crude oxidized Leu A ($[M+H]^{+1}$ calcd: 3929.8; found: 3929.5) and pure negative peptide ($[M+H]^{+1}$ calcd: 1990.1; found 1992.7). FIGS. 8B and 8D depict RP-HPLC chromatograms of Leu A and negative peptide. The HPLC method used was 10-100% acetonitrile/water in 70 min with a flow rate of 1 mL/min on Vydac C18 semi-preparative column.

FIG. 9A depicts a schematic showing the steps involved in covalent peptide immobilization using APTES (3-aminopropyl)triethyloxysilane) on a glass surface. The method involves (1) silicon substrate cleaning using piranha solution, (2) generation of silane layer using optimized APTES (2%, v/v) solution, (3) treatment with glutaraldehyde solution which reacts with peptide to give covalently immobilized peptide on solid surface.

FIGS. 9B and 9C depicts fluorescence comparison between FITC-labeled peptide (10 μL) immobilized via covalent conjugation (glutaraldehyde; FIG. 9B) versus non-covalent interaction (FIG. 9C) on a glass surface. After spotting peptide on both the slides (6 spots per slide), the spots were allowed to dry. Thereafter, each slide was washed by dipping into Milli Q water and the slides were imaged using Bio-rad Chemidoc imager (λex 304 nm and λem 607 nm, green filter).

FIG. 10A: First, AuNC was prepared by mixing HAuCl$_4$ (10 μL, 1, 10 or 100 mM) with a constant concentration (3 μL, 100 mM) of 3-MPA (3-mercaptopropionic acid) solution. AuNC (13 μL) was spotted on glass surface with bacteria ($10^4$/10 μl) or no bacteria present, and fluorescence was imaged using Chemidoc imager (λex 302 nm and λem 607 nm, green filter). FIG. 10B: Next, AuNC was prepared by mixing HAuCl4 (10 μL, 10 mM) with 3-MPA solution (3 μL, 10 or 100 mM). AuNC (13 μL) was spotted on glass surface with bacteria ($10^4$/10 μl) or no bacteria present, and fluorescence was imaged as above.

FIG. 11A: First, HAuCl$_4$ (3, 5, 9, or 11 μL; 10 mM) was spotted on bacteria or no bacteria followed by constant volume of MPA (3 μL, 100 mM). Fluorescent intensity of each spot was measured. Each bar represents the mean of three repetitions. FIG. 11B: Next, a fixed volume of HAuCl$_4$ (9 μL, 10 mM) was spotted on bacteria or no bacteria followed by varying volumes of MPA (1, 3, 5, and 9 μL, 100 mM). Fluorescent intensity of each spot was measured. Each bar represents the mean of three repetitions.

DETAILED DESCRIPTION

Disclosed herein is a peptide-based biosensor for detection of bacteria species in contaminated samples.

In an assay for *Listeria* species, an antibacterial peptide, Leucocin A, is immobilized on a glass surface to specifically trap *Listeria*. Leucocin A is a potent ligand for protein receptors on *L. monocytogenes* species, and has a minimum inhibitory concentration (MIC) in the low nanomolar range against these bacteria. Bacteria bound or trapped by Leucocin A are washed to remove non-specific binding followed by labelling with highly fluorescent gold nanoclusters (AuNC). The gold nanoclusters are made in situ by directly spotting HAuCl$_4$ and 3-mercaptopropionic acid (MPA) on top of bacteria on a glass slide. Finally, the fluorescently labeled bacteria are imaged to detect *Listeria* in a given sample, with a detection limit of $2\times10^5$ cfu/mL. The biosensor assay is portable, simple, fast (45-50 minutes), can be performed by non-experts, and has a potential to be used as a screening tool for *L. monocytogenes* in food and pharmaceutical products.

The high mortality rate (>20%) of *Listeria monocytogenes* makes this pathogen a serious threat to human life. Disclosed herein is a peptide-based platform for detection of *Listeria* using the class IIa bacteriocin, Leucocin A (LeuA). Leucocin A is highly specific for *Listeria* species. The bacteria are trapped using Leucocin A and labeled with gold nanoclusters (AuNC) for detection in a rapid assay.

Figure 1:
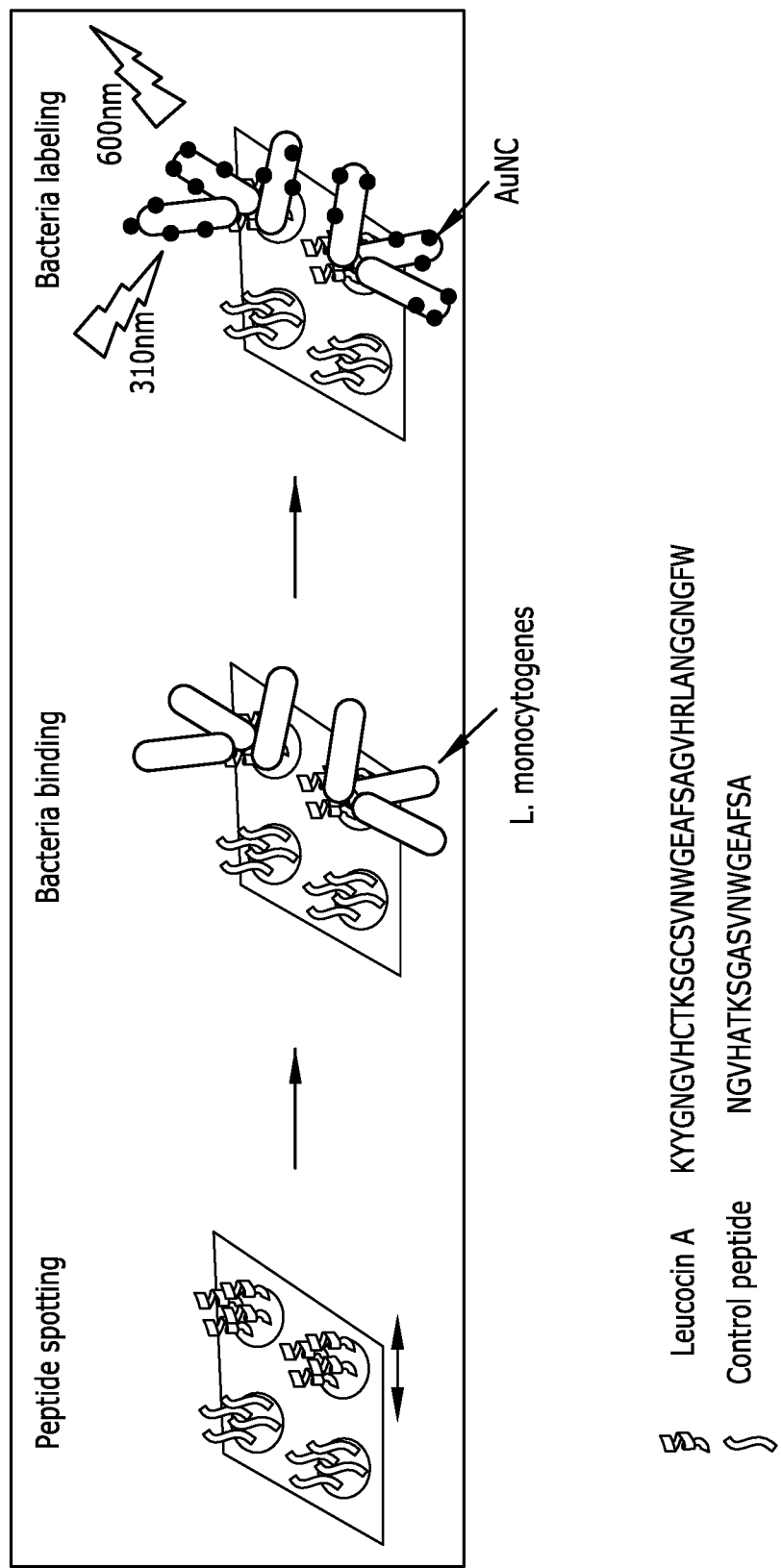
FIG. 1 depicts a schematic showing steps for specific detection of *Listeria monocytogenes* using Leucocin A (LeuA) and gold nanoclusters (AuNCs). First, 37-residue Leu A (SEQ ID NO:1) (or control peptide, SEQ ID NO:2) was spotted (immobilized) on a glass slide. In the second step, a sample (with or without bacteria) was spotted on the peptide and left (to dry) for 20 minutes at room temperature. The slide was washed and AuNCs were spotted to label bound bacteria. After drying for about 20 minutes, the fluorescence intensity of AuNC bound with bacteria was read using a Bio-rad Chemidoc imager ($\lambda$ex 304 nm and $\lambda$em 607 nm, green filter) to detect bacteria.

The method for rapid and specific detection of *L. monocytogenes* is based on combining the molecular recognition capability of Leucocin A and fluorescence labelling ability of AuNC. Leucocin A has an amphipathic helical motif in the C-terminal region (FIG. 1) that causes it to bind specifically to *L. monocytogenes* strains and closely related bacteria. Specifically LeuA binds to the mannose phosphotransferase system (PTS) permease present on the surface of these bacteria. Leucocin A is immobilized on a surface to trap target bacteria from a given contaminated sample and the peptide-bound bacteria are then labeled for fluorescent detection. Metal nanoclusters, and specifically AuNC, have attracted attention as fluorescent agents due to several characteristics including excellent photo-stability, biocompatibility, and ultra-small size (<3 nm). The synthesis of AuNC is quick and easy, and the resulting nanoclusters present excellent emission properties. Different ligands or capping agents are used to stabilize nanoclusters including biomolecules like single amino acids, DNA, proteins, small thiol-containing molecules like 3-mercaptopropionic acid (MPA), or even polymers. As shown in FIG. 1, the biosensor assay allows detection of *L. monocytogenes* after it is bound to the peptide (LeuA) on a solid surface. The disclosed biosensor can detect *Listeria* in a short time (45-50 mins) from a small sample volume (10 μL) with a limit of detection of $2\times10^5$ cfu/mL.

First, 37-residue LeuA (SEQ ID NO:1) is spotted (immobilized) on a glass slide. In the second step, a sample (with or without bacteria) is spotted on the peptide and left for 30 minutes at room temperature. The slide is washed and AuNC are spotted to label bound bacteria. The fluorescence intensity of AuNC bound with bacteria is read using Bio-rad Chemidoc imager (λex 302 nm and λem 607 nm, green filter) to detect bacteria.

As used herein, the terms "spot" or "spotted" refers to depositing a quantity of sample on a substrate in a specified location on the substrate. As used herein, samples may be spotted on a substrate in a general grid pattern with a clear boundary around each "spot" which does not contain any peptide. A substrate can include any number of "spots" to detect bacteria in multiple samples.

The biosensor assay developed herein is unique as it allows detection of *L. monocytogenes* in about 45-50 minutes and does not require trained personnel. The sample is added on the peptide spots on the glass slide. Peptide spotted (conjugated) glass slides can be previously prepared and stored. Once the sample is dry on the glass surface (about 20 minutes), it is washed and labeled with AuNC by adding HAuCl$_4$ and stabilizer MPA. The slide is then imaged under a fluorescence imager to determine the presence of *Listeria*. Currently the limit of detection (LOD) is around $2\times10^5$ cfu/mL. The use of different ligands (stabilizers), such as peptides may increase the fluorescence (quantum yield) of bound bacteria. The biosensor assay allows detection of *Listeria* from milk sample and this can be extended to other ready-to-eat food products such as hot dogs and cheese. In addition, the use of peptides specific for other bacteria, like microcin J25 for *E. coli* and microcin N for *Salmonella* spp., can allow the biosensor to detect any other specific bacterial strain.

The selective detection of *L. monocytogenes* species in milk samples is reported here claiming limit of detection (LOD) of $2\times10^5$/mL. An antibacterial peptide is applied to develop a selective biosensor specifically for the bacterial species. The main advantages of the proposed technique are being quick, requiring small sample volume, simple one-pot synthesis of AuNC, and being selective for the bacterial species. This technique can be considered as a primary screening in clinical and research laboratories.

Thus, disclosed herein are assays for determining the presence of specific bacteria in a sample, the method comprising immobilizing a ligand specific for the bacteria to a substrate, contacting a sample suspected of having the bacteria with the immobilized ligand and incubating for a period of time such that the bacteria present in the sample binds to the ligand and are immobilized on the substrate, contacting the bound bacteria with a detection reagent, and detecting the presence of bacteria in the sample.

The substrate on which the ligand is immobilized can be a variety of glass or silica substrates (surfaces) including, but not limited to (a) glass microscope slides or other glass surfaces, (b) glass fiber mats or filters, (c) glass microchannel arrays, (d) glass capillary channels, (e) fiber optic glass microchannels, and other glass or silica substrates. Thus, within the scope of the present disclosure are substrates which will allow screening of large sample volumes more suitable for commercial application of the biosensor assay. In some embodiments, the substrate is glass. In yet other embodiments, the substrate is a porous membrane such as a polyvinylidene difluoride (PVDF) or cellulose membrane.

The ligand can be any binding agent which is specific for a species, or strain, of bacteria. In one embodiment, the bacteria is a *Listeria* species and the ligand is Leucocin A. In some embodiments, the bacteria is *Listeria monocytogenes*. In one embodiment, the bacteria is a *Salmonella* species and the ligand is microcin N (GDPLADPNSQI-VRQIMSNAAWGAAFGARGGLGG-MAVGAAGGVTQTVLQGAAAHMPVNV PIPKVPMGPSWNGSKG; SEQ ID NO:3).

The sample can be any material which is suspected of having been contaminated with *Listeria monocytogenes*. Exemplary samples include, but are not limited to, ready-to-eat food, dairy products, fresh fruit, fresh vegetables, meat, fish, processed food, etc. If the sample is in liquid form, such as milk, the sample can be used directly, or diluted with an aqueous diluent such as water or saline. If the sample is a solid material, such as fruit, meat, cheese, etc., the sample may be converted into a liquid form by grinding and mixing with an aqueous diluent such as water or saline to form a liquid, suspension, or slurry which can be deposited on the immobilized ligand.

The detection reagent comprises gold nanoclusters (AuNC).

In some embodiments, the incubation period is from about 20 minutes to about 120 minutes. In other embodiments, the incubation period is from about 20 minutes to about 90 minutes, about 20 minutes to about 60 minutes, or about 20 minutes to about 40 minutes. In some embodiments the incubation period is about 20 minutes.

In some embodiments, after application of each reagent or sample to the substrate, the reagent or sample is allowed to dry prior to proceeding to the next step. This drying period can be from about 10-60 minutes, such as from about 15-45 minutes, about 20-30 minutes, or about 20 minutes. The drying step can be at any temperature. In some embodiments, the drying step occurs at room temperature, about 20 to 25° C.

In embodiments where the substrate is a membrane, unbound peptide and bacteria can be removed by washing the membrane with an aqueous solution under vacuum.

The immobilized bacteria are then detected by any method able to measure fluorescence. In one embodiment, the AuNC are detected by absorption at about 290-310 nm and fluorescence at about 600 nm. In some embodiments, the absorption is about 300 nm. In some embodiments, the absorption is about 302 nm. In some embodiments, the absorption is about 304 nm.

Also disclosed herein are kits for detecting the presence of *Listeria* in a sample, the kits comprising a LeuA-bound substrate, AuNC, or reagents to prepare AuNC, and additional reagents and instructions for performing an assay disclosed herein. Further disclosed herein are kits for detecting *Salmonella* in a sample, the kits comprising a microcin N-bound substrate, AuNC or reagents to prepare AuNC, and additional reagents and instructions for performing an assay disclosed herein.

EXAMPLES

Example 1

Peptide-Based Glass Biosensor Utilizing Fluorescent Gold Nanoclusters for Detection of *Listeria monocytogenes*

Methods

Fmoc-amino acids, tryptophan preloaded Wang resin (loading 0.59 mmol/g), alanine preloaded Wang resin (loading 0.57 mmol/g), and O-(1H-6-chlorobenzotriazole-1-yl)-N,N,N',N'-tetramethyluronium hexafluorophosphate (HCTU) were purchased from Novabiochem. All solvents and chemicals including triisopropylsilane, dichloromethane (DCM), dimethylformamide (DMF), N-methylmorpholine (NMM), diethyl ether, acetonitrile, 3-mercaptopropionic acid (3-MPA), chloroauric acid ($HAuCl_4$), trifluoroacetic acid (TFA), (3-aminopropyl) triethoxysilane (APTS), glutaraldehyde, Luria broth (LB), agar and soy broth were obtained from Sigma-Aldrich. Piperidine (20% in DMF) was purchased from Protein Technology (Tucson, Ariz.). α-Cyano-4-hydroxycinnamic acid (CHCA) matrix was purchased from Fluka. Milli-Q system was used for ultra-pure water.

Synthesis was performed on automated peptide synthesizer Tribute from Protein Technologies (Tucson, Ariz.). HPLC system used was Prominence-i (Shimadzu, Kyoto, Japan). ChemiDoc™ XRS+system (California, USA) was used to record fluorescence intensity. UV-2600 UV-Vis spectrophotometer and RF-5301PC spectrofluorophotometer (Shimadzu) were used to obtain absorption and fluorescence spectrum, respectively. Mass spectrometry was performed on Bruker's autoflex speed high-performance MALDI-TOF system.

Bacteria. Bacterial strains, *Listeria monocytogenes* ATCC 43256, *L. monocytogenes* ATCC 19116, *Staphylococcus aureus* ATCC 29213, and *Bacillus cereus* ATCC 14579 were purchased from the American Type Culture Collection (ATCC). *Escherichia coli* DHα was obtained from Jason Yamaki Laboratory (Chapman University School of Pharmacy). *L. monocytogenes* Type I was obtained from Rosalee Hellberg laboratory at the Schmid College of Science and Technology (Chapman University).

AuNC synthesis and characterization. AuNC were synthesized using the method of Sahoo with some modifications (Sahoo, et al., ACS Appl Mater Interfaces 6:712-24, 2014). Briefly, $HAuCl_4$ (10 mM in water) was mixed with 3-MPA (100 mM in water) in a 3:1 volume ratio, and the absorption/emission spectra of synthesized AuNC were recorded using UV-vis fluorescence spectrophotometer. AuNC was further characterized for its mass using MALDI-TOF mass spectrometry by spotting AuNC (2 μL) without matrix on MALDI plate.

Optimization of AuNC for labeling bacteria immobilized on glass surface. Optimization of AuNC for fluorescent labelling of bacteria was done using a non-pathogenic E. coli DHα strain. First, the glass surface was spotted with bacteria ($10^4$ cfu/10 uL) or water (10 uL, no bacteria) and the spots were allowed to dry for 20 minutes. Each spot was done in triplicate (bacteria and water). Next, $HAuCl_4$ (10 μL, 1, 10 or 100 mM) was spotted on top of the bacteria spot followed by spotting 3-MPA (3 μL, 100 mM). The spots were again allowed to dry for about 20 minutes, and fluorescence was imaged using Chemidoc imager (λex 302 nm and λem 607 nm, green filter). The experiment was repeated by spotting a fixed concentration of $HAuCl_4$ (10 μL, 10 mM) and varying concentration of 3-MPA solution (3 μL, 10 or 100 mM), and the spots were imaged for fluorescence as above.

Next, the concentration of $HAuCl_4$ and MPA was further optimized by varying volumes of each when spotted on bacteria for fluorescent labelling of bacteria on the surface. Briefly, bacteria ($10^4$ cfu/10 uL) or water (10 uL, no bacteria) was spotted in triplicates on a glass surface and the spots were allowed to dry. Next, different volumes of $HAuCl_4$ (3, 5, 9, or 11 μL; 10 mM) was spotted on top of the bacteria or water spot followed by a constant volume of MPA (3 μL, 100 mM). Fluorescent intensity of each spot was then measured. Similarly, a fixed volume of $HAuCl_4$ (9 μL, 10 mM) was spotted on the bacteria or water spot followed by varying volumes of MPA (1, 3, 5, or 9 μL, 100 mM). Each sample (spot) was assayed in triplicate and then repeated twice. All subsequent experiments were repeated similarly.

Peptide Synthesis. Leucocin A (37-mer; SEQ ID NO:1) and negative peptide (20-mer; SEQ ID NO:2) (see FIG. 1) were synthesized based on Fmoc solid phase peptide synthesis (Fmoc-SPPS) on Wang resin (0.1 mmol scale) using automated peptide synthesizer (Tribute, Protein Technology). Synthesis of Leucocin A (LeuA) was done on Wang resin pre-loaded with tryptophan, while synthesis of negative peptide was done using Wang resin preload with alanine. Fmoc-Trp-Wang resin (169 mg, 0.1 mmol) or Fmoc-Ala-Wang resin (175 mg, 0.1 mmol) was added to the glass reaction vessel (RV). Resin swelling was done automatically with nitrogen blow and mechanical shaking in DMF for 30 min. All amino acids were coupled in sequence. For each coupling, HCTU (2.5 equiv) and NMM (1.2 equiv) was mixed with amino acid (3 equiv) in DMF (3 mL) for 75 minutes. Fmoc removal was done using 20% piperidine in DMF. An extra DCM washing in the final step of synthesis was added to have resin ready for peptide cleavage. After the 10th amino acid, the coupling time was doubled (2.5 h) to increase the yield. For LeuA, after the 20th amino acid, double coupling was used (two consecutive coupling steps). After the 30th amino acid, in addition to the double coupling, the assigned time for each coupling was increased to 4 hour from 2.5 hours. Cleavage of peptides was done manually. The cleavage cocktail used was 95% TFA (9.50 mL), 2.5% TIPS (250 μL) and 2.5% (250 μL) water. The peptides were precipitated using cold diethyl ether (20 mL). After centrifugation, the supernatant was removed and the remaining sample was dissolved in ACN/water. Linear LeuA was oxidized in an overnight reaction in 50 mM Tris buffer (pH 8.4), in addition 20% DMSO was added to increase peptide solubility and facilitate oxidation. The solution was stirred overnight at room temperature while exposed to the air. The oxidation was confirmed using MALDI-TOF analysis and reversed-phase HPLC. The peptides were purified on C18 Vydac semi-preparative HPLC column (1×25 cm, 5 μm) using i-Prominence Shimadzu HPLC system. A gradient of ACN/water from 10 to 100% in 60 minutes with a flow rate of 1 mL/min was used. The pure peptides, LeuA and negative peptide were characterized using RP-HPLC (tR=40 min and 37 min, respectively) and MALDI-TOF mass spectrometry (FIG. 8). Based on the HPLC chromatograms both peptides were >95% pure, and were obtained in good yields with LeuA at 60% and negative peptide at 75% yield.

Bioactivity. LeuA and negative peptide were checked for activity using agar plate inoculated with L. monocytogenes Type I. Briefly, a TSB agar plate was spotted with different concentrations of peptide (2.3, 0.23, and 0.023 mM, dissolved in water) with a spot volume of 10 μL. Then the 6 mL soft agar inoculated with 60 μL L. monocytogenes (overnight culture, undiluted) was plated over the TSB agar. The plate was incubated at 37° C. and zone of inhibition was checked after 24 hours.

Peptide Immobilization. Two different methods were evaluated to immobilize the peptides on glass surface. A FITC-labeled 11-mer peptide (FITC-WxEAAYQkFLA; SEQ ID NO:4; wherein k is D-lysine and x is D-norleucine) was used as a representative peptide to determine the immobilization method. In the first approach, the peptide was covalently immobilized on the glass surface (Fisher Scientific, L×W: 75×25 mm). This method involved three steps, first of which was to etch the glass surface using piranha solution for 20 min. Piranha solution was prepared by mixing 3 parts sulfuric acid with 1 part 30% hydrogen peroxide. The second step was the synthesis of a silane layer using optimized (3-aminopropyl)triethyloxysilane (APTES, 2%, v/v) solution. The slide was dipped in the 2% APTES in a pre-heated toluene solution for 1 hour, after which the slide was dried on a hot surface (80° C.) for 1 hour. Finally, the slide was treated with 2.5% glutaraldehyde in PBS for 20 minutes. The glutaraldehyde acted as the linker for the peptide immobilization. FITC (10 μL)-labeled peptide was then spotted on the functionalized slide. After air drying, the slide was washed for 20 seconds using MilIQ water.

The next approach was based on non-covalent immobilization of peptide on the glass slide. FITC-labelled peptide was spotted directly on the glass slide surface (10 μL) and was left to dry. Then the slide was washed with MilIQ water for 20 seconds. In both experiments (covalent and non-covalent), six identical spots were made, the fluorescence was quantified using Chemidoc imager and the average was calculated for each method.

Detecting L. monocytogenes using AuNC on glass surface. An aqueous solution of Leu A (10 μL, 0.13 mM) was spotted on a glass slide (~4 mm diameter) in triplicate. The peptide spots were allowed to air dry (~20 min). This was followed by spotting bacteria L. monocytogenes ATCC 43256 (10 μL, $10^4$ cells) or no bacteria (10 μL water) on top of the peptide spot. The glass slide was then dipped in MilIQ water for 10 seconds to remove all non-bound bacteria. The slide was allowed to air dry and finally AuNC (12 μL) was deposited on each spot. AuNC (12 μL) alone was also spotted as a control. The mean fluorescence intensity was recorded using Chemidoc imager. The experiment was repeated three times.

Optimization of peptide concentration. The bio-sensor was optimized by testing different LeuA concentrations. The slide was spotted with 10 µL of varying peptide concentrations (0, 0.013, 0.025, 0.064, or 0.13 mM). The peptide spot was allowed to air dry for 20 min. Next, bacteria (*L. monocytogenes* ATCC 19116) was spotted at a constant concentration (10 µL, $10^4$ cfu). After drying, the slides were dipped in MilIQ water for 10 seconds. Lastly AuNC (12 µl) was spotted to quantify the fluorescence intensity of the spots.

Sensitivity and selectivity of the biosensor. To obtain the limit of detection (LOD), the biosensor assay was performed with varying number of bacteria in 10 µL sample. An overnight culture of *L. monocytogenes* ATCC 19116 was diluted to obtain samples with 0, 200, 1000, 2000, and 10000 cfu/10 µL. A glass slide was prepared with peptide spots (Leu A, 0.13 mM, 10 µL) as descried above and bacteria (10 µL) were spotted on the peptide spot followed by AuNC labeling and fluorescence recording using Chemidoc imager.

The selectivity of the biosensor assay was tested with three *L. monocytogenes* strains (ATCC 43256, ATCC 19116, and Pat Type 1), *B. cereus* ATCC 14579, *S. aureus* ATCC 29213, *S. enterica*, and *E. coli* DHα. Water (no bacteria) was used as a control. Another control used was with a negative peptide (24-mer) spot, and *L. monocytogenes* 19116 was used. The biosensor assay was performed as described above.

Detection of *Listeria monocytogenes* in spiked milk sample. A spiked milk sample was prepared using milk (3.5% fat, 1 mL) diluted with water (9 mL). *L. monocytogenes* 19116 was added to the diluted milk to obtain a bacterial concentration of $10^4$ cfu/10 µL. Water was used as a control. The biosensor assay was performed on the spiked milk sample as described above.

Results

Figure 2A:
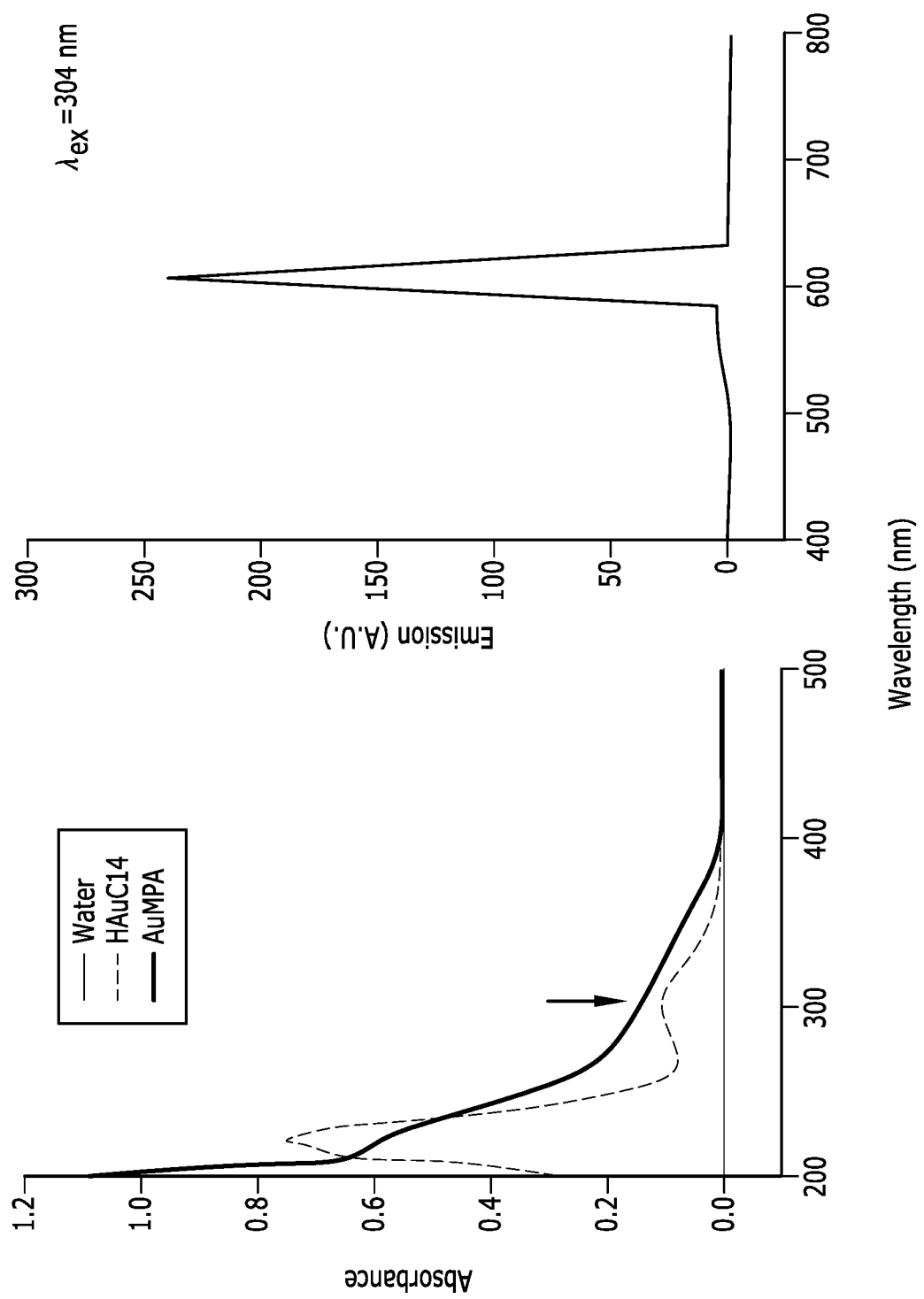
FIG. 2A-B depicts characterization of MPA-AuNC.
Figure 2B:
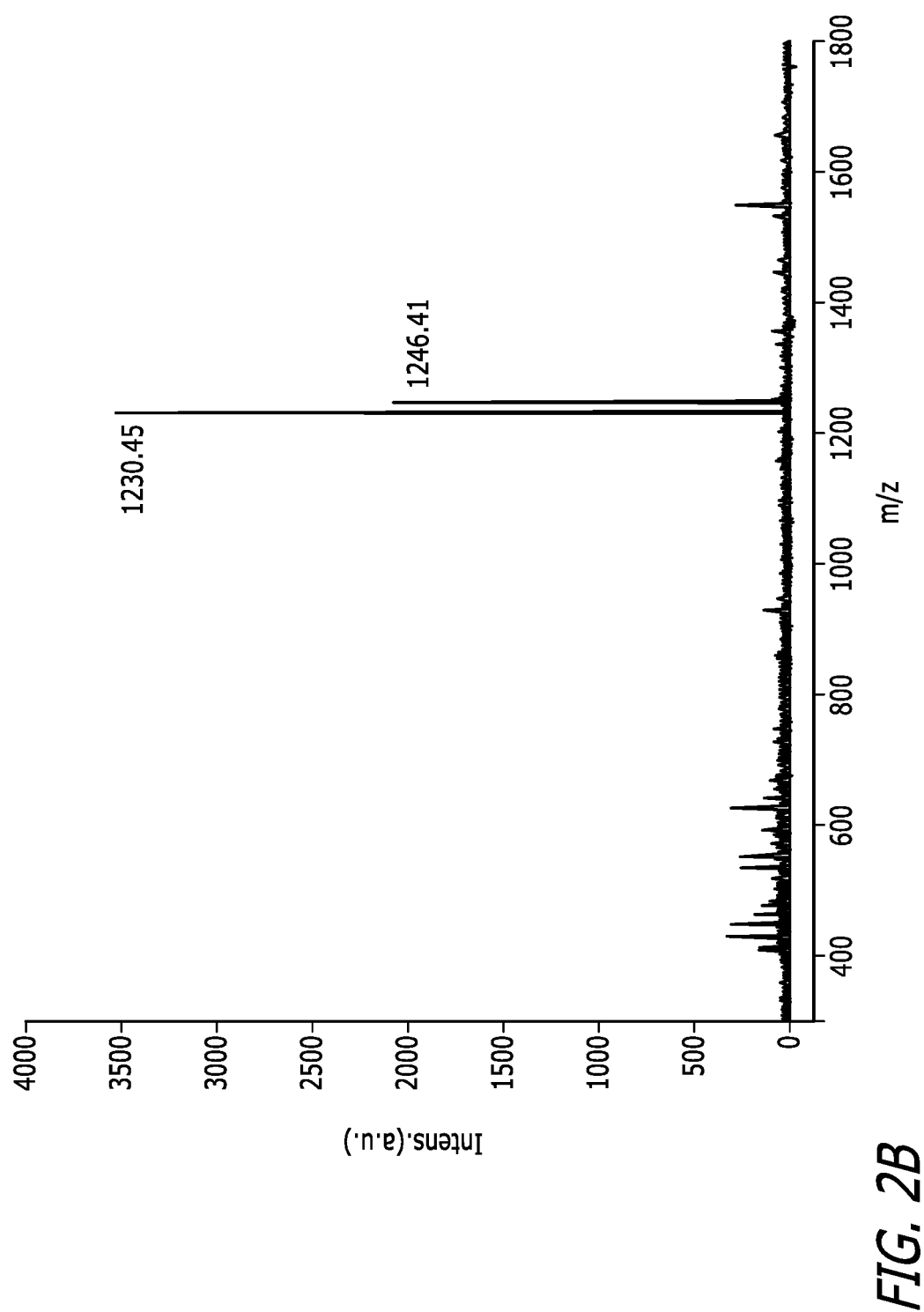

Preparation of AuNC using MPA as a ligand. Gold nanoclusters (AUNC) were synthesized using $HAuCl_4$ with 3-MPA as the stabilizer. Thiol-containing molecules like 3-MPA are the most commonly used stabilizers for both nanoclusters and nanoparticles as this strategy allows one-pot facile synthesis. A solution of $HAuCl_4$ is mixed with 3-MPA in about 1:3 molar ratio and the synthesized AuNC are characterized using fluorescence spectroscopy. As shown in FIG. 2A, the AuNC show maximum absorption at ~300 nm with emission around 600 nm. The nanoclusters have light yellow color under visible light, however when excited under UV light, AuNC emit red fluorescence. Further characterization was done using MALDI-TOF mass spectrometry. There is a dominant peak observed for AuNC at 1230.5 Da, followed with 1246.4 Da (FIG. 2B). These peaks at 1230.5 Da and 1246.4 Da were calculated to be AuNC composed of 4 Au and 4 MPA atoms with sodium $[Au_4(MPA)_4+Na]$ and potassium $[Au_4(MPA)_4+K]$, respectively. The AuNC were stable for a week at room temperature and for several weeks in the refrigerator. Existing detection techniques that use AuNC either involve long and complicated methods for preparation of AuNC or sometimes give clusters that are not stable over time. The presently disclosed methods overcome this problem.

Peptide immobilization on glass surface. We previously showed that class IIa bacteriocin LeuA or fragments (24-mer or 14-mer) derived from the C-terminal amphipathic helical region of Leu A bind specifically to *L. monocytogenes* and closely related Gram-positive strains (Azmi S. et al. ACS Comb Sci, 17:156-163, 2015; Etayash H et al. Langmuir 29:4048-4056, 2013). The peptides or fragments were covalently immobilized on glass surfaces, and the binding between the peptide and bacteria was sensed using fluorescence microscopy (using labeled bacteria), microcantilever bending (label-free detection), or impedance spectroscopy (label-free detection).

Figure 9A:
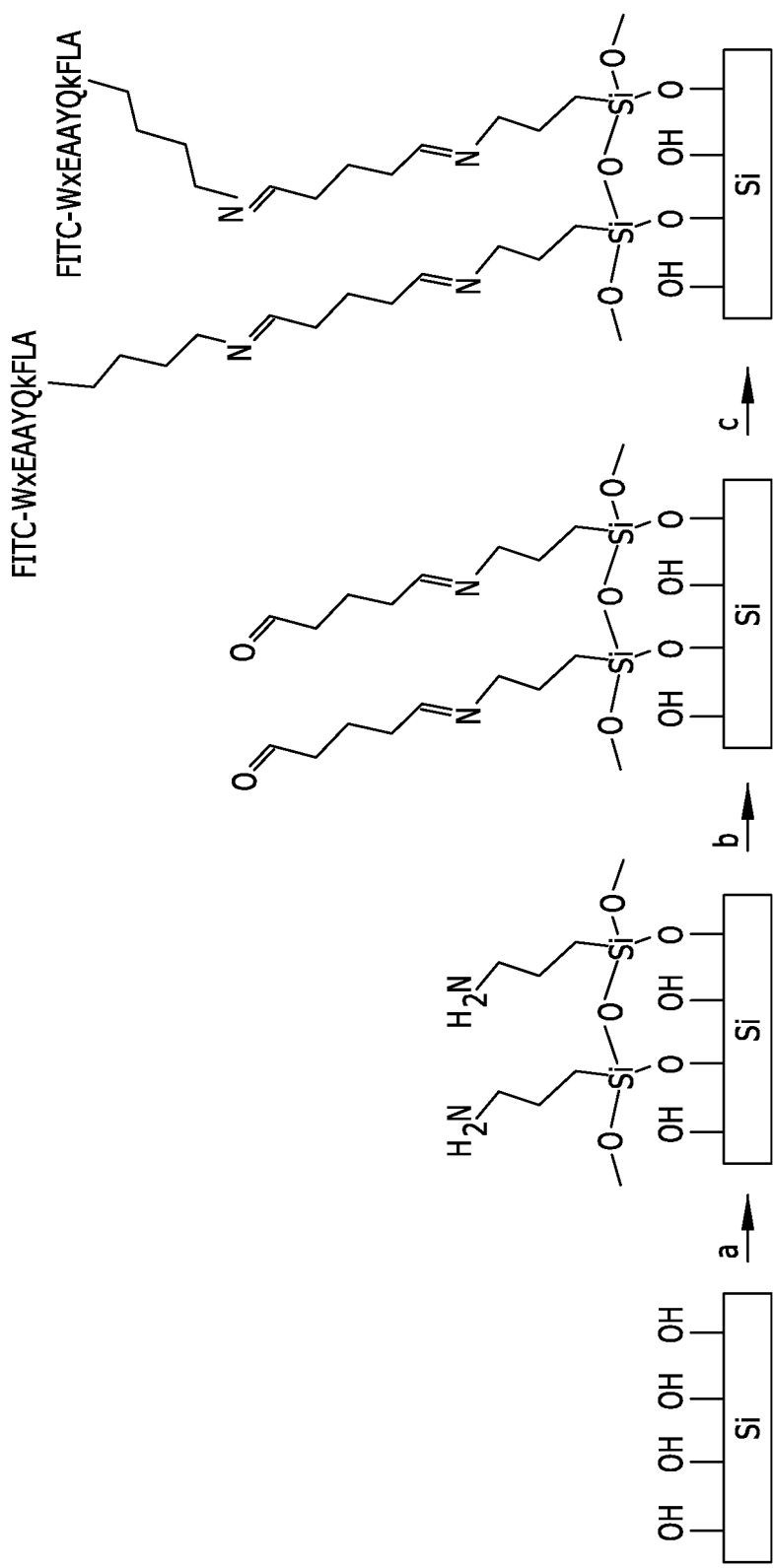
FIG. 9A-C.
Figure 9B:
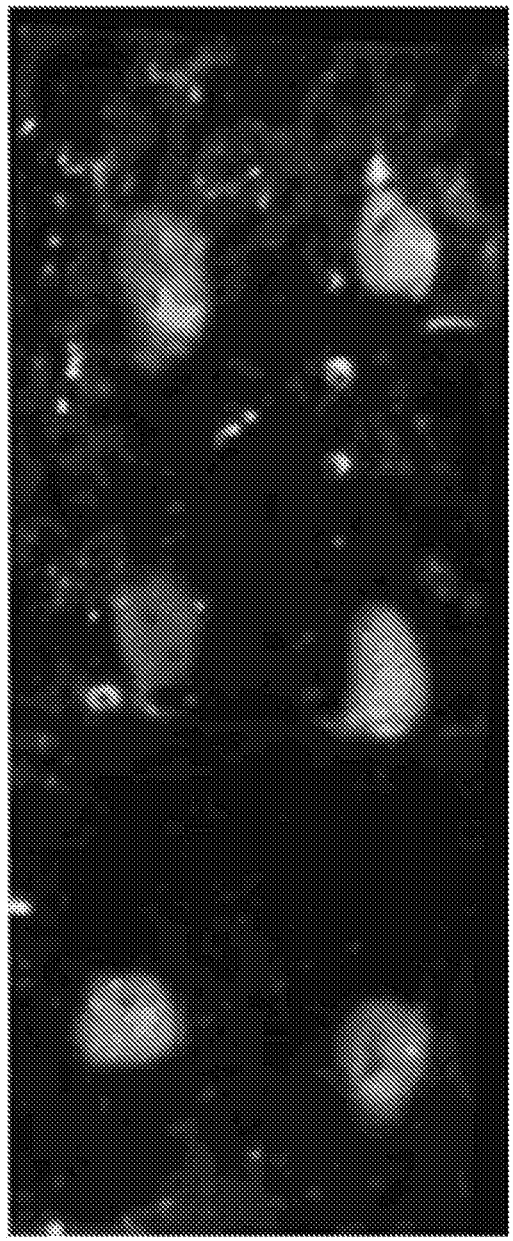
Figure 9C:
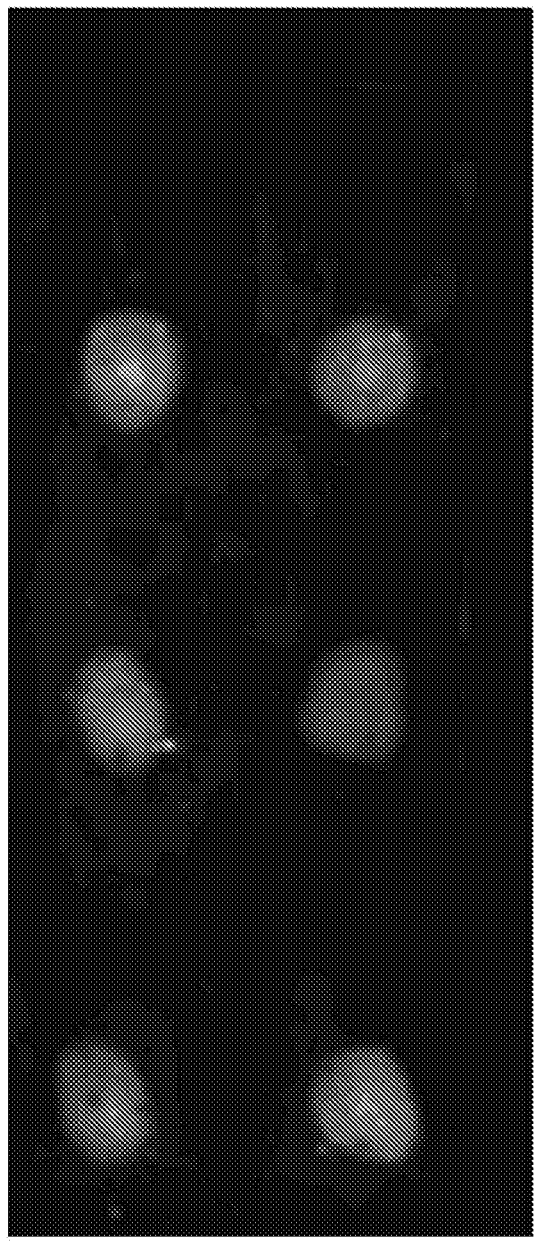

In the presently disclosed assay, full length LeuA (SEQ ID NO:1) was used for binding *L. monocytogenes*. A short sequence (20-mer; SEQ ID NO:2) derived from LeuA which is known not to bind *L. monocytogenes* was used as a negative control peptide. Using the bioactivity plate assay, it was confirmed that LeuA was active against *L. monocytogenes*, whereas the control 20-resdiue sequence was inactive. LeuA was non-covalently immobilized on a glass surface by spotting a small sample (10 µL) directly on the surface. Non-covalent immobilization was fast and easy and deposited the same amount of peptide as the covalent immobilization. Covalent immobilization involved several steps, namely, etching the glass, modifying the surface with APTES followed by treatment with glutaraldehyde and peptide (FIG. 9A). A FITC-labeled peptide was immobilized using both the covalent and non-covalent methods, and the mean fluorescence intensity (MFI) of the surface bound peptide was compared (FIG. 9B-C). The average MFIs of the six spots for the two peptide immobilization methods were 23927±4902 and 19708±3299, respectively. This suggests that both methods give similar peptide density (average MFI was not significantly different) upon immobilization. For all the subsequent experiments, non-covalent immobilization by directly spotting the peptide on a glass surface was used. Peptide-immobilized glass slides could be stored in refrigerator or freezer (−20° C.) for months to be used in future assays.

Figure 10A:
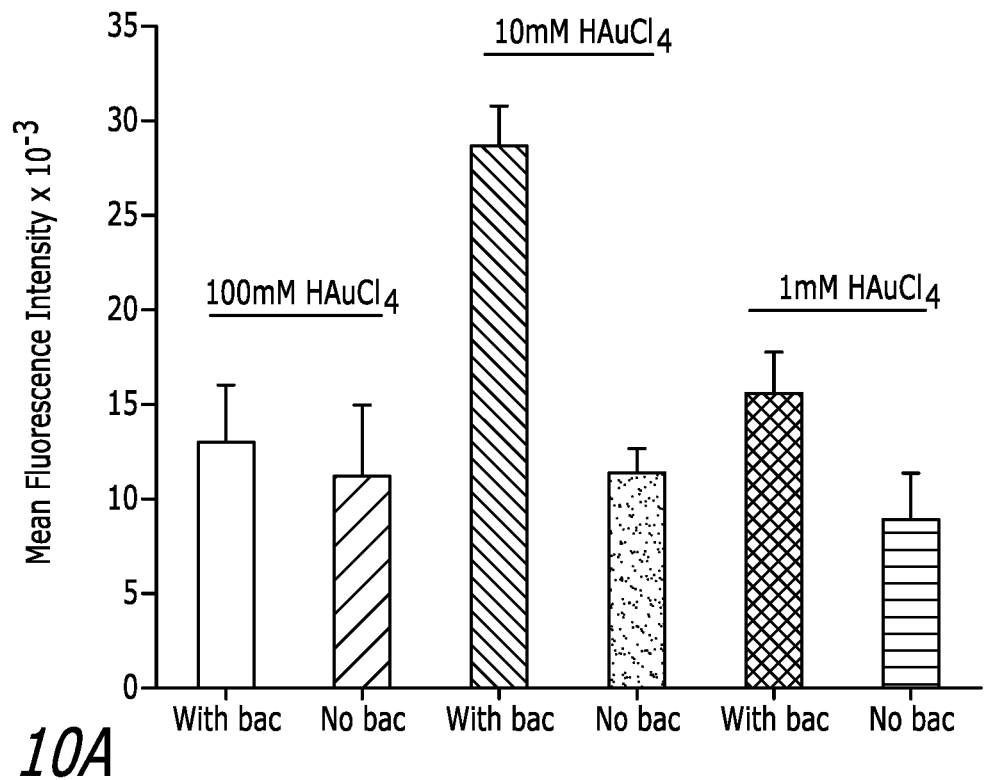
FIG. 10A-B depicts optimization of AuNC synthesis for fluorescent labelling of *E. coli* DHα.
Figure 10B:
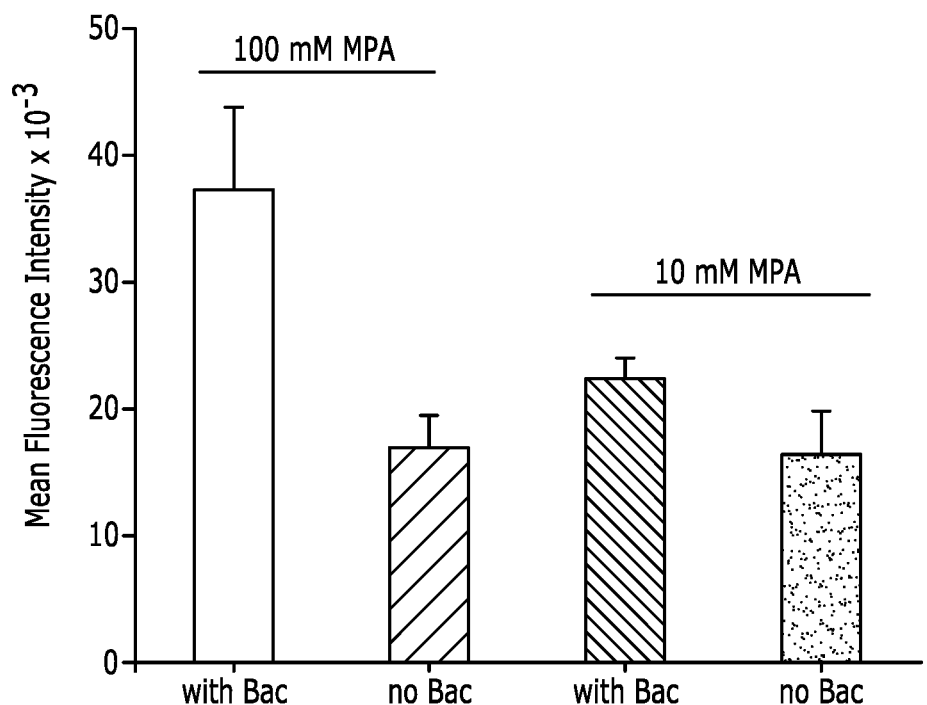
Figure 11A:
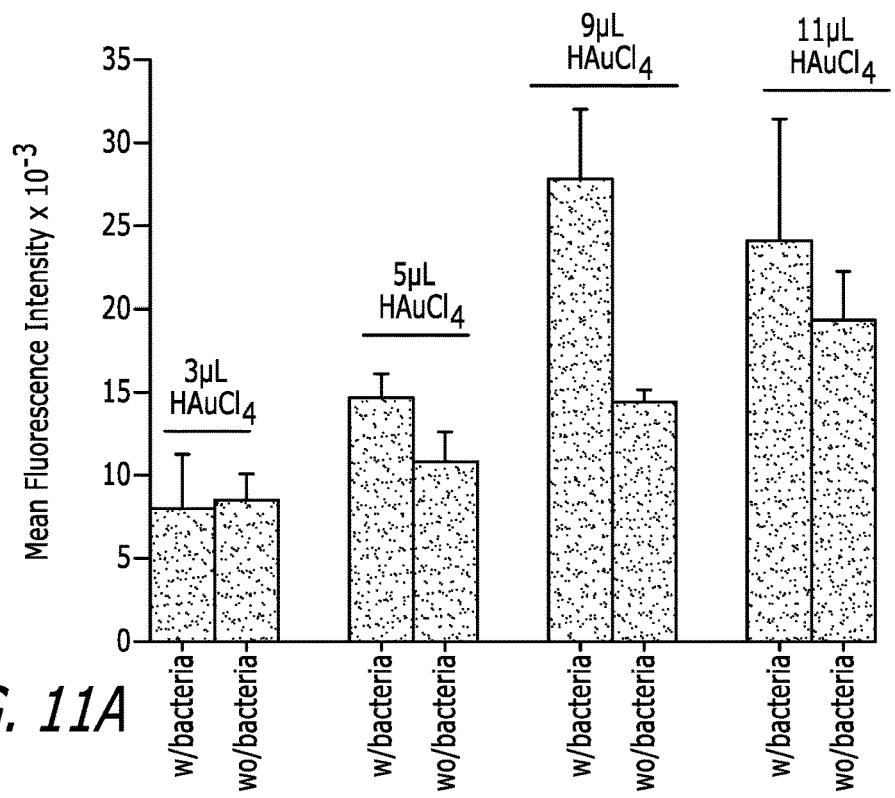
FIG. 11A-B depicts optimization of HAuCl$_4$ and MPA ratio for fluorescent labelling of *E. coli* DHα. The bacteria (10 μL, 10,000 CFU) or no bacteria (10 μL water) were spotted to bind the peptide followed by bacterial labeling with AuNC.
Figure 11B:
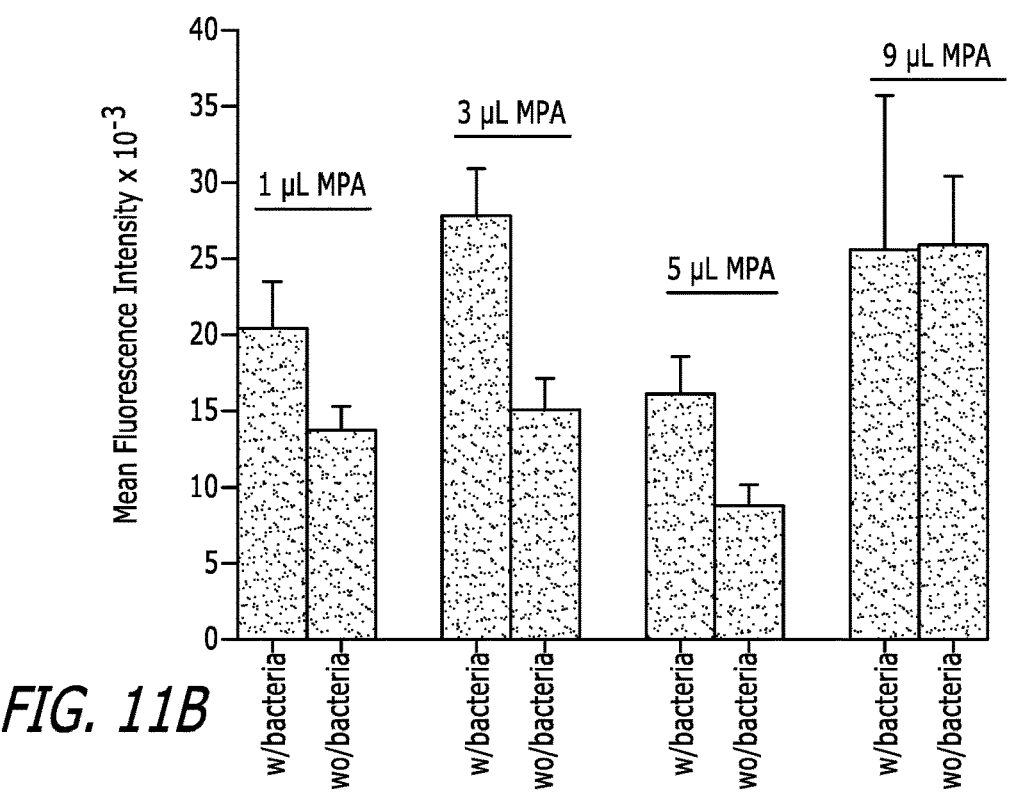

Labeling bacteria with AuNC. AuNC were used to label the immobilized bacteria. A bacterial solution (10 µL) was spotted on a glass slide and bacteria were labeled by adding $HAuCl_4$ (9 µL, 10 mM) and MPA (3 µL, 100 mM) on top of the bacteria spot. The concentrations of $HAuCl_4$ and MPA were optimized to obtain maximum fluorescence (FIGS. 10 and 11). In general, bacteria (10 µL, $10^4$ cells) were spotted on surface and were labeled with $HAuCl_4$ (9 µL, 10 mM) and MPA (3 µL, 100 mM). The molar ratio of $HAuCl_4$ and MPA used is the same as one used in making AuNC in solution (FIG. 2).

Figure 3:
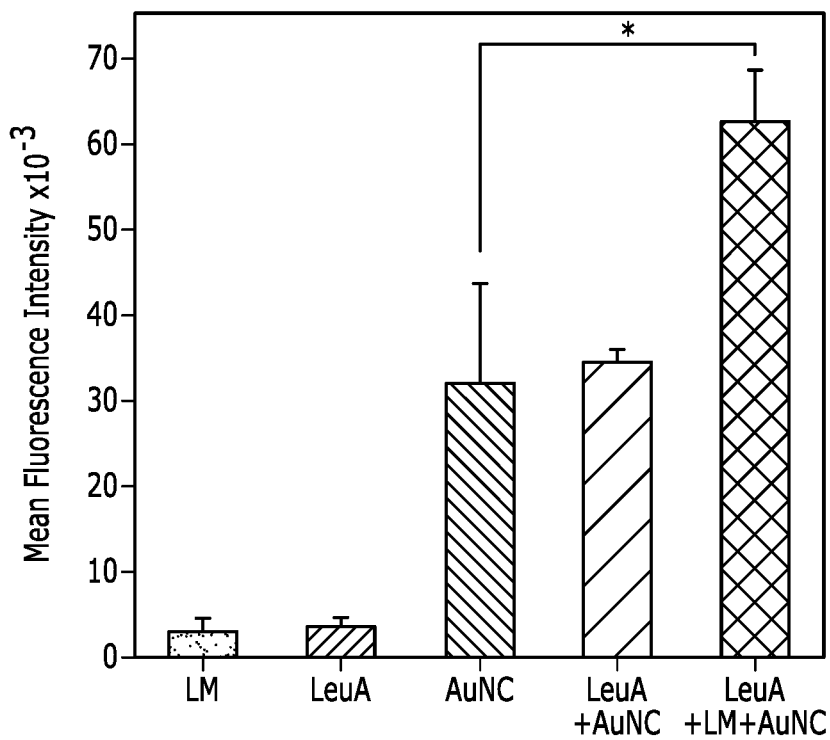
FIG. 3 depicts comparison of AuNC fluorescence on glass surfaces. Defined spots (with 4 mm diameter) on a glass surface are prepared by spotting (i) AuNC (12 μL) alone, (ii) Leu A peptide (10 μL, 0.13 mM) followed by AuNC (12 μL), and (iii) Leu A (10 μL, 0.13 mM) followed by bacteria *L. monocytogenes* ATCC 43256 (LM, 10 μL, $10^4$ cells) and then AuNC (12 μL). Each spot was allowed to dry before spotting the next material. In addition, peptide (Leu A) and bacteria were also spotted alone as controls. The experiment was repeated three times.

Next, AuNC were used to label bacteria bound to peptide to develop the biosensor assay. A glass slide was spotted with peptide (LeuA), and bacteria or no bacteria (water) was spotted on the peptide. Finally, the spots were labelled by AuNC by adding $HAuCl_4$ and MPA. AuNC was also spotted alone for comparison of fluorescence between the AuNC alone and AuNC-labelled bacteria. As shown in FIG. 3, AuNC-labeled bacteria showed significantly higher fluorescence (MFI 62390±5975) compared to AuNC alone (MFI 31860±11608). Also, AuNC addition to peptide spots showed no increase in AuNC fluorescence (MFI 34352±1812). It was observed that the peptide and bacteria show no auto-fluorescence at >600 nm.

Figure 4:
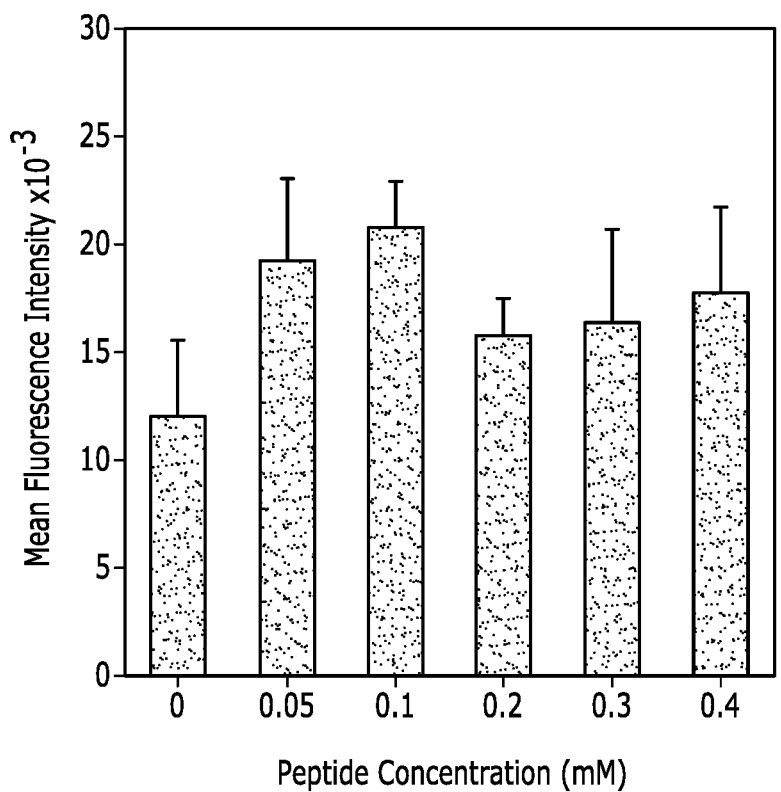
FIG. 4 depicts the fluorescence response of bound bacteria with increasing Leu A peptide concentration per spot. Leu A (10 μL) was spotted on glass slide followed by *L. monocytogenes* ATCC 43256 ($10^4$ cells/10 μL) and AuNC (12 μL). The fluorescence intensity of AuNC-labelled bacteria was read using Bio-rad Chemidoc imager ($\lambda$ex 302 nm and $\lambda$em 607 nm, green filter).

Assay optimization. In order to trap higher number of bacteria from the sample to increase the limit of detection, the peptide concentration was optimized for each spot on a glass slide. The slide was spotted (10 µL) with varying peptide concentrations (0.05-0.4 mM), and the quantity of bound bacteria from the sample ($10^4$ cfu/10 µL) was estimated based on the fluorescence intensity of each spot. The results show increased fluorescence intensity with increased peptide concentration up to 0.1 mM, indicating that more bacteria were retained with higher peptide concentration on the substrate (FIG. 4). At peptide concentrations higher than 0.1 mM, there was a small drop in fluroescence at concentrations of 0.2-0.4 mM. The spot with a peptide concentration of 0.13 mM showed highest fluorescence (21275±2177) and this peptide concentration was used for all subsequent experiments.

Figure 5:
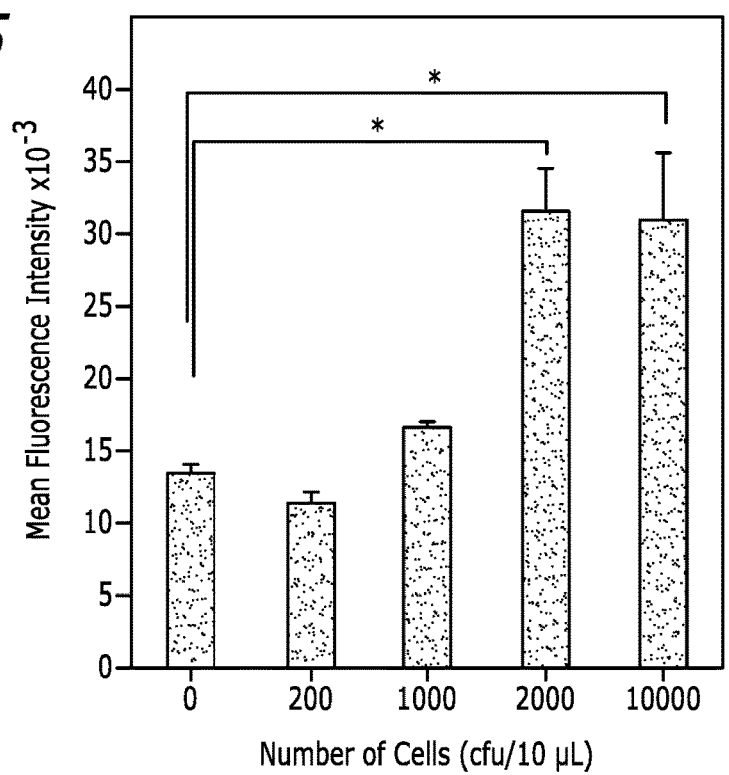
FIG. 5 depicts the fluorescence response of bound bacteria with increasing bacterial concentration (*L. monocytogenes* ATCC 19116) per spot. Peptide Leu A (10 μL, 0.13 mM) was spotted on glass slide followed by bacteria (10 μL) and AuNC (12 μL). The fluorescence intensity of AuNC-labelled bacteria was read using Bio-rad Chemidoc imager ($\lambda$ex 304 nm and $\lambda$em 607 nm, green filter). Statistical significance was denoted by *($P<0.05$).

Estimation of the limit of detection. To obtain the LOD of the peptide-based biosensor assay, LeuA (0.1 mM) was spotted on slides, followed by varying concentrations of bacteria (0, 200, 1000, 2000, and 10000 cfu/10 µL), after which AuNC was applied to label the bound bacteria. As shown in FIG. 5, a sample containing 2000 cfu or higher per spot showed significantly higher fluorescence compared to the water alone. Sample containing 10000 cfu bacteria showed similar fluorescence (30842±4696) as the 2000 cfu sample (31473±2932) suggesting that the peptide spot was saturated with bacteria and did not allow binding of any additional bacteria above 2000 cfu. From these results, it can be estimated that the LOD for the bio-sensor is around 2000 cfu/10 µL or $2 \times 10^5$ cfu/m L.

Previously bacteria were detected at a concentration of $10^5$ cfu/mL using a microcantilever method and $10^6$ cfu/mL using CyQuant-labeled bacteria. The other methods allowed detection at much lower concentration. For instance, with impedance spectroscopy and more recently with a biomaterial microcantilever, a LOD of $10^3$ cfu/mL was acheived. In addition, labelling peptide-bound bacteria with propidium iodide and detection with confocal microscopy allowed detection at $10^3$ cfu/mL. However, most of these methods require sophisticated equipment like a microcantilever or confocal microscopy which mandates trained personnel.

Figure 6:
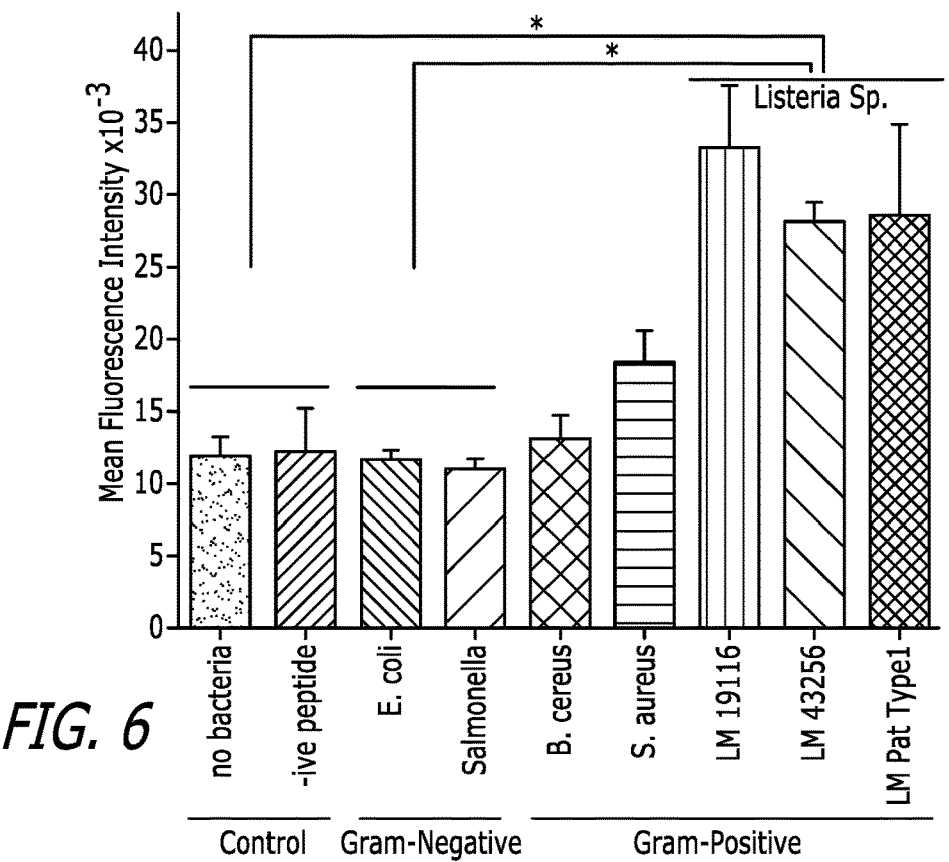
FIG. 6 depicts selectivity of the assay toward *L. monocytogenes* strains. The mean fluorescence intensity of different bacteria ($10^4$ cells/10 μL) labeled using MPA-AuNC (12 μL) is compared. Bacteria were trapped (bound) to the surface via binding to Leu A peptide or negative control peptide. Each sample was spotted in triplicate and the experiment was repeated three times on three different days. Statistical significance was denoted by *($P<0.05$).

Assay selectivity. The selectivity of the bio-sensor assay was tested with a total of seven different bacteria. Out of the seven, three were different strains of *L. monocytogenes*. Other bacteria used were Gram-negative *E. coli* (non-pathogenic) and *S. enterica* Serovar Enteritidis, and Gram-positive *S. aureus* and *B. cereus*. A total of five Gram-positive and two Gram-negative strains were selected which are all common food pathogens. As shown in FIG. 6, the *Listeria* strains were easily detected using the biosensor assay showing significantly higher fluorescence (range 28000-33000) than the control sample (12000±2000). These strains did not bind to the negative control (20-mer) peptide as observed from the fluorescence (12164±2937). Both the Gram-negative bacteria showed no binding to LeuA (12000±800). *B. cereus* showed no binding (13000±1600) as well, whereas *S. aureus* ATCC 29213 showed some binding to the peptide with a fluorescence of 18000±2100. Low binding of *S. aureus* ATCC 13565 to Leu A was also observed previously. In addition, a monoclonal antibody against *L. monocytogenes* showed weak cross-reactivity to *S. aureus* in an ELISA. These results suggest that among the seven bacteria tested, LeuA binds *listeria* strains selectively and *listeria* can be detected based on the AuNC fluorescence of peptide bound bacteria.

Figure 7:
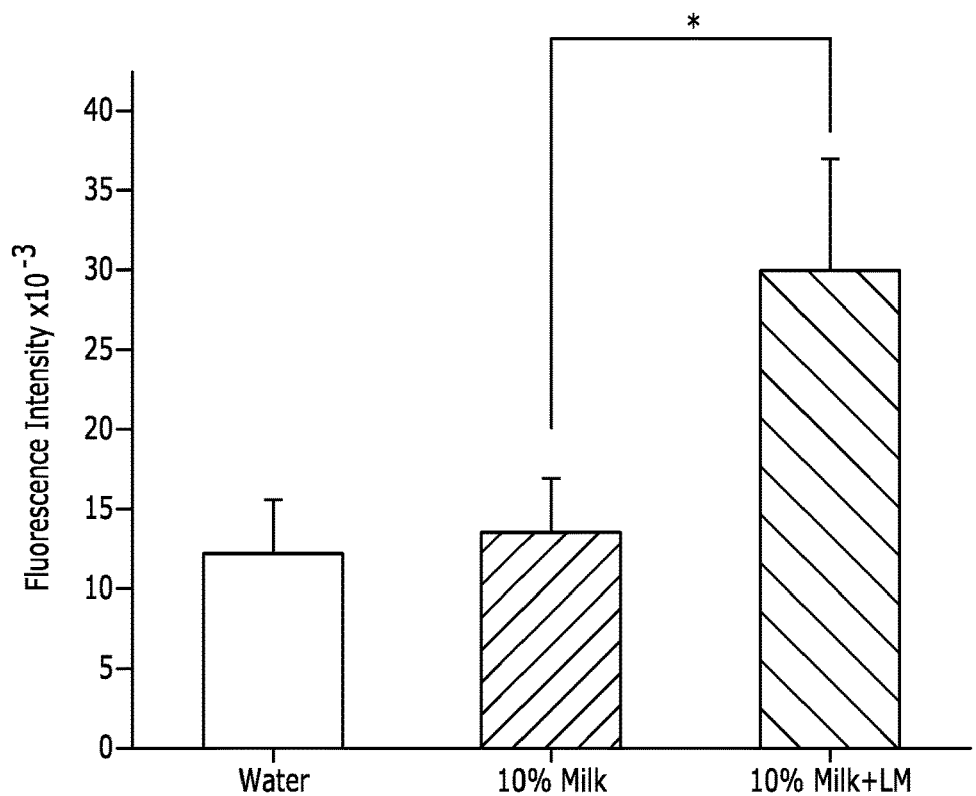
FIG. 7 depicts the validation of the assay using spiked milk samples. Milk samples (10%) were prepared by mixing whole milk with MilliQ water, and were spiked with *L. monocytogenes* ATCC 19116 at a concentration of $10^3$ cfu/μL. Water, milk sample, or spiked milk samples (10 μL) were spotted on peptide (0.13 mM) immobilized on a glass surface and were labelled with MPA-AuNC (12 μL). The fluorescence intensity of each spot was imaged using Chemidoc imager. Statistical significance was denoted by *($P<0.05$).
Figure 8A:
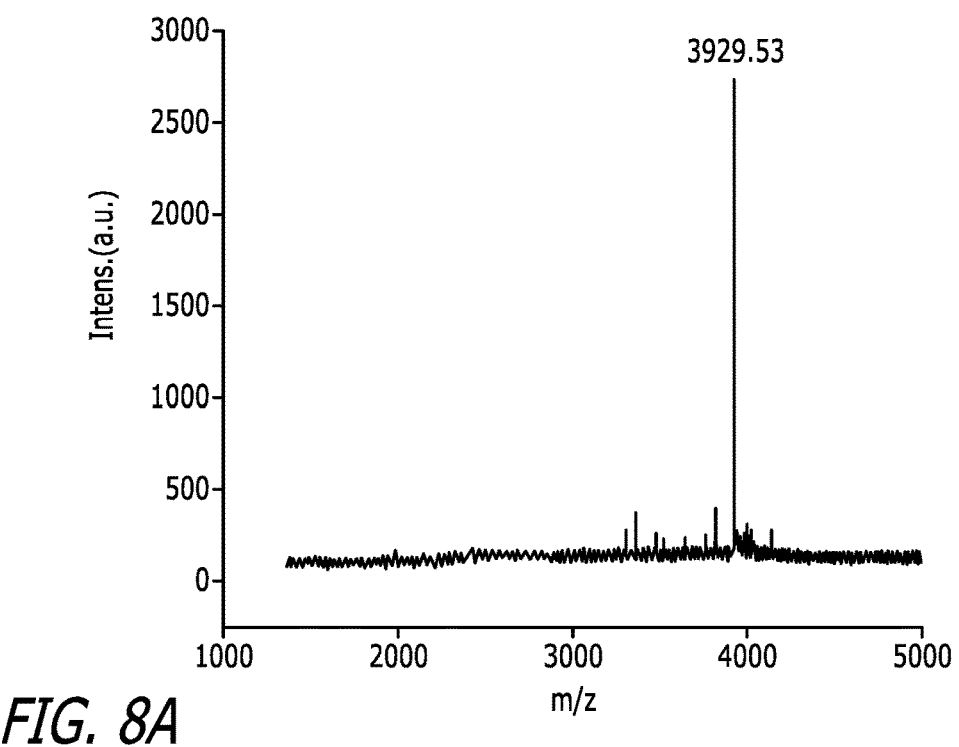
FIG. 8A-D.
Figure 8B:
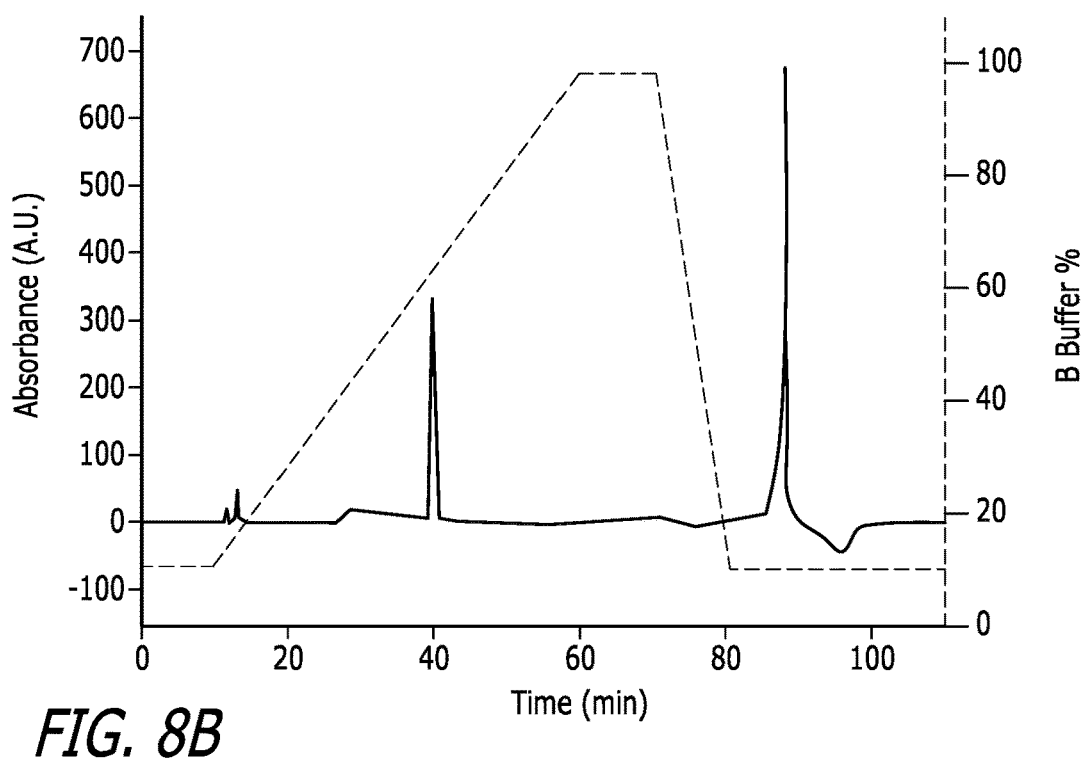
Figure 8C:
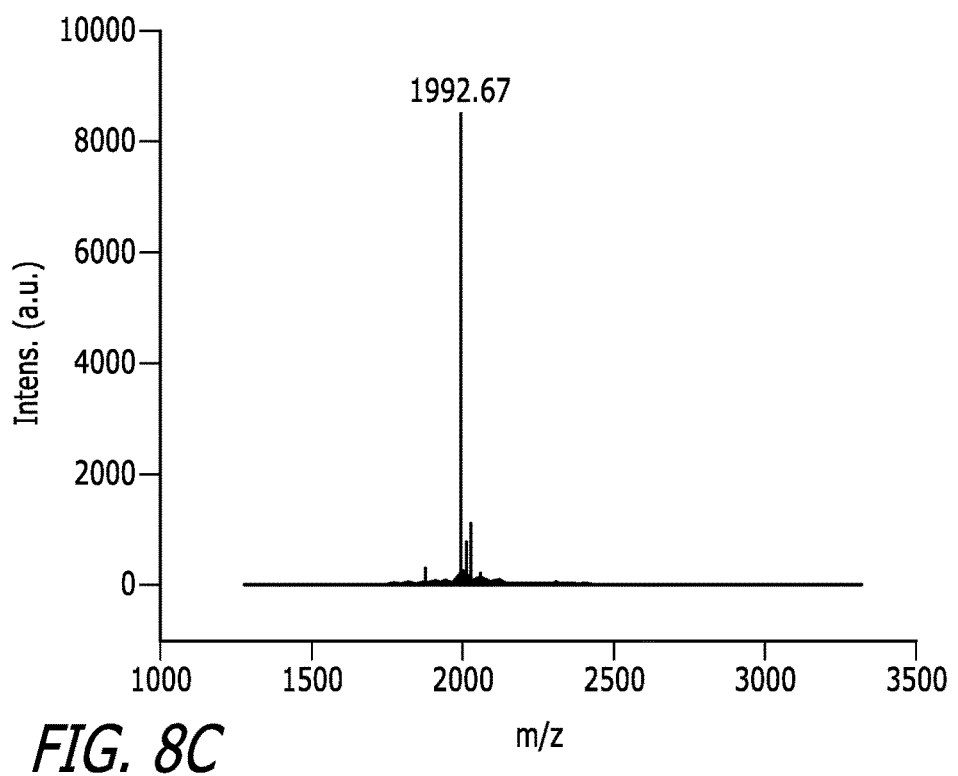
Figure 8D:
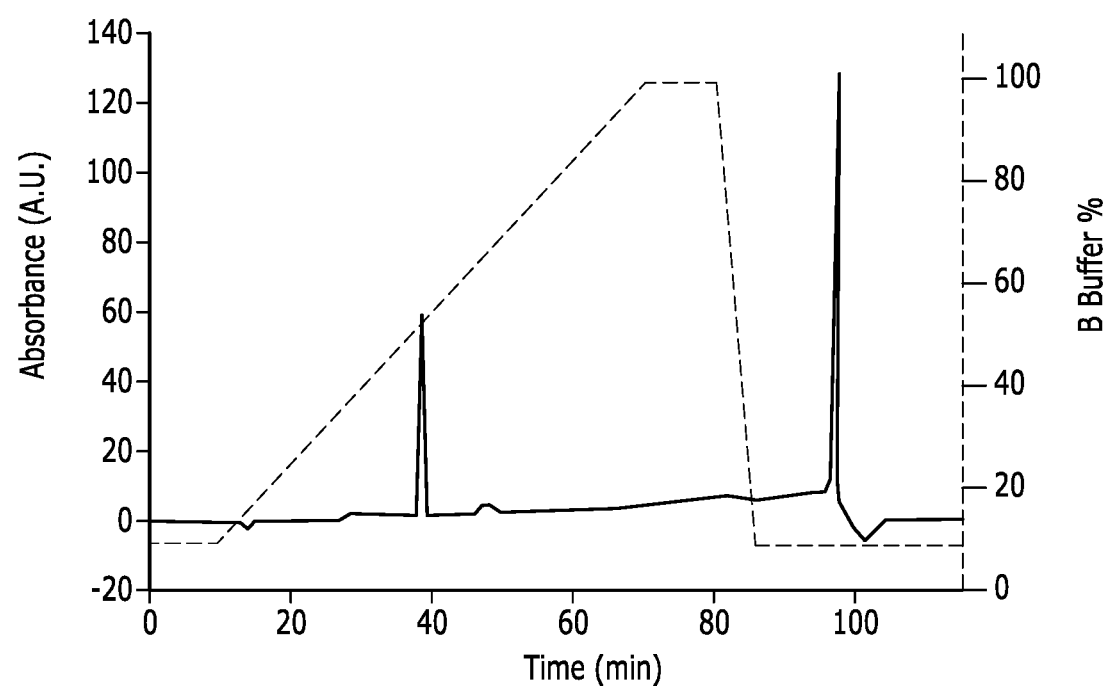

Detection of *Listeria monocytogenes* in spiked milk sample. *L. monocytogenes* is commonly found in contaminated food. Here milk spiked with *Listeria* was used to emulate a contaminated food sample. Whole milk (3.5% fat) was diluted with water and was spiked with $10^3$ cells/µL *L. monocytogenes*. After analyzing the sample with the biosensor assay, the spiked milk sample showed significantly higher fluorescence compared to the milk alone (FIG. 7).

Example 2

Peptide-Conjugated Porous Membrane Detection of *Listeria*

In Example 1, a glass surface having LeuA peptide immobilized thereon was used to bind and detect bacteria in water samples. This allowed analysis of a small sample volume (~10 µL) as the sample was spotted on the glass surface and allowed to dry on the glass surface before detection of bacteria. In the experiments below, a porous membrane was conjugated with LeuA peptide. The peptide-conjugated membrane was exposed to the sample and, since it is porous, it allows analysis of large sample volumes such as 5 mL or more. Samples contaminated with bacteria are allowed to pass through the membrane and the bacteria are trapped by binding to the peptide on the membrane surface. Later, bound bacteria are labelled with gold nanoclusters (AuNC) for detection by fluorescence.

Figure 12:
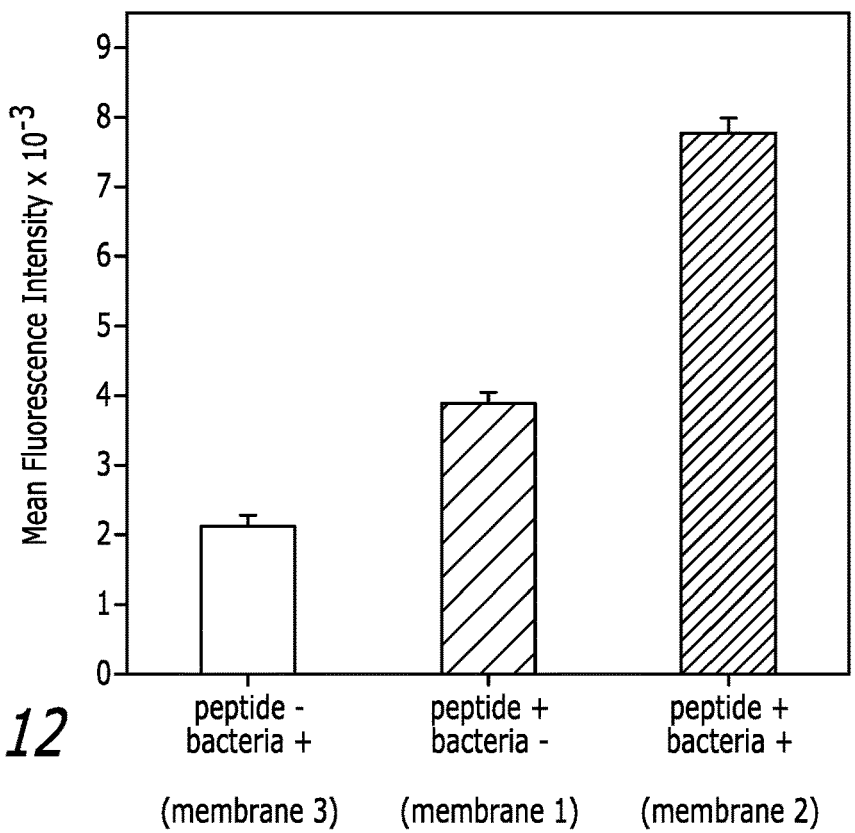
FIG. 12 depicts the fluorescence response of sample with or without bacteria on a PVDF membrane. The membrane was first coated with a monolayer of peptide (peptide+; membranes 1 and 2), followed by exposure to bacteria (5000 cfu in 500 μL water; bacteria+) or no bacteria (500 μL water; bacteria−). Membrane (membrane 3) with no peptide (peptide−) was also used as a control. All three membranes were exposed to (treated with) AuNC before reading the fluorescence using BioRad imager. The experiment was repeated twice.

Detection of bacteria using AuNC on membrane. A low-fluorescence polyvinylidene difluoride (PVDF) membrane (Thermo Scientific) was cut into 3 small circular pieces (~0.75 cm radius). The circular membrane was placed on a membrane holder which was connected to a side arm Erlenmeyer flask with vacuum. Each membrane was first washed with copious amount of water by allowing water to filter through the membrane using a gentle vacuum. Membranes 1 and 2 were then conjugated with peptide LeuA by delivering 100 µL peptide solution (0.012 mM). The peptide was allowed to bind the membrane for ~20 minutes and then excess, unbound peptide was removed by vacuum. Next, the peptide-conjugated membranes were exposed to samples with bacteria (5000 cfu *Listeria* innocua ATCC 33091 in 500 µL water; membrane 1) or without bacteria (500 µL water; membrane 2). A membrane without bound peptide (membrane 3) was used as a control and was also exposed to bacteria (5000 cfu in 500 µL water). Finally, all three membranes were reacted with AuNC (500 µL, 100 µL stock diluted to 500 µL with water) to label the bound bacteria. Excess AuNC was removed by vacuum and the membrane was allowed to dry for ~15-20 mins before fluorescence imaging. The fluorescence of each membrane was read using BioRad Imager (FIG. 12). The results show that there is an increased fluorescence when the sample contains bacteria (7776) versus sample without bacteria (3880). The fluorescence for the peptide-conjugated membrane alone (no bacteria; membrane 2) could be due to the binding of AuNC with the peptide. This represents baseline fluorescence (3880) and any increase in fluorescence from baseline represents the presence of bacteria as shown in FIG. 12. In this experiment with porous membrane, non-pathogenic bacteria *Listeria* innocua were used (which are very similar to *L. monocytogenes*) due to convenience. Later experiments with the membrane were performed with *L. monocytogenes* ATCC 19116.

Figure 13:
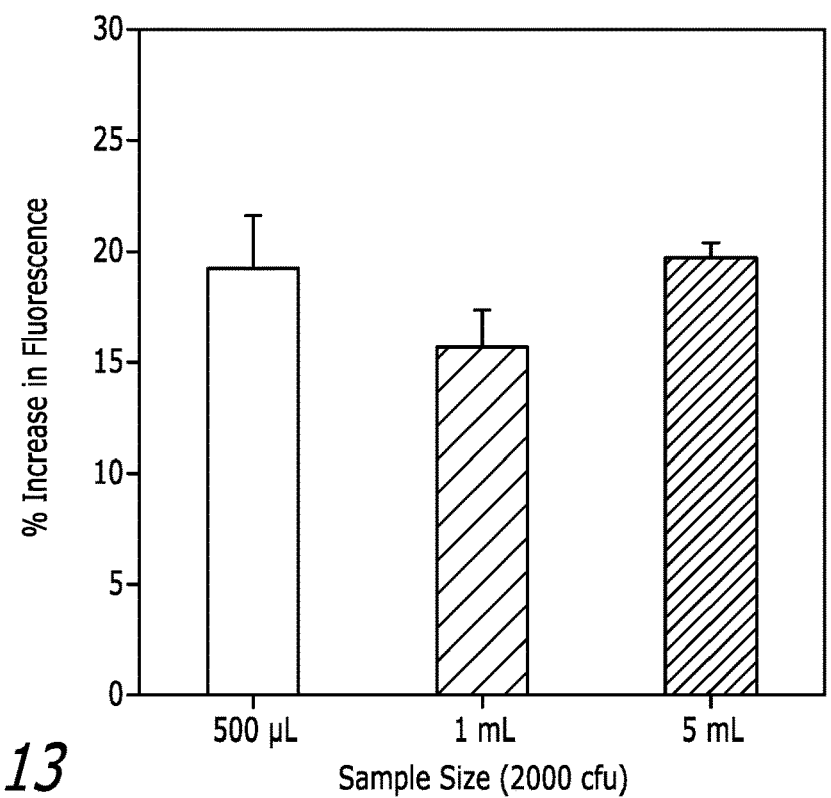
FIG. 13 depicts the percent increase in fluorescence for samples containing same number of *L. monocytogenes* ATCC 19116 (2000 cfu) in different volumes (500 μL, 1 mL and 5 mL). The experiment was repeated twice.

Detection of *L. monocytogenes* from different sample volumes. Six circular membranes conjugated with peptide LeuA were prepared as described above. Peptide-conjugated membranes were exposed to three samples of different volumes (500 µL, 1 mL, and 5 mL) each containing same number of *L. monocytogenes* ATCC 19116 (2000 cfu). Membranes were also exposed to samples (water) with no bacteria (500 µL, 1 mL, and 5 mL) to serve as controls. After passing the samples through the membranes, all membranes were reacted with AuNC (500 µL, 100 µL stock diluted to 500 µL with water) to label the bound bacteria. Excess AuNC from each membrane was removed by vacuum and the membrane was allowed to dry for ~15-20 mins before fluorescence imaging. The fluorescence of each membrane was read using a BioRad Imager. The results (FIG. 13) show that for all three samples with different volumes and the same number of bacteria (2000 cfu), the percent (%) increase in fluorescence was in the same range (15-20%). The increase in fluorescence was calculated using the following equation.

$$\% \text{ increase in fluorescence} = \frac{MFI \text{ of contaminated sample} - MFI \text{ of sample (water only)}}{MFI \text{ of sample (water only)}}$$

Based on this experiment, the assay can be used for detection of *L. monocytogenes* from samples of different volumes.

Figure 14:
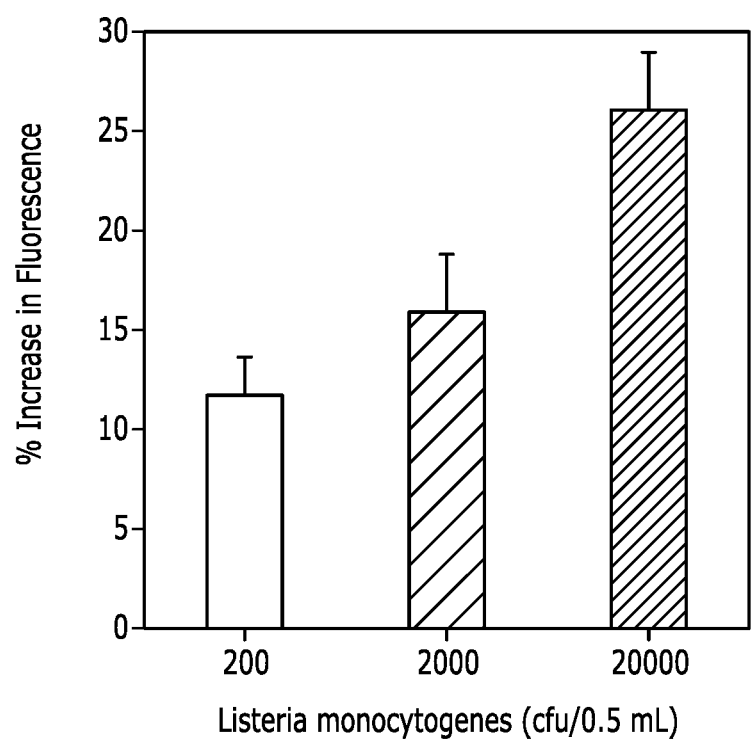
FIG. 14 depicts The percent increase in fluorescence for samples containing different number of *L. monocytogenes* ATCC 19116 (200, 2000, or 20000 cfu) in 500 μL water. The experiment was repeated twice.

Estimation of the limit of detection for *L. monocytogenes*. Four circular membranes conjugated with peptide LeuA were prepared as described above. The membranes were exposed to samples (500 µL) containing different numbers of *L. monocytogenes* ATCC 19116 (0, 200, 2000, or 20000 CFU). The rest of the assay was performed as described above. The results (FIG. 14) show that fluorescence signal increases with an increase in the number of bacteria. The percent increase in fluorescence for samples (500 µL) containing 200, 2000, and 20000 cfu *L. monocytogenes* was 11.7%, 15.9%, and 26.1%, respectively. Based on these results, it can be estimated that the limit of detection for the biosensor assay using peptide LeuA-conjugated membrane is around 200 cfu.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An assay for determining the presence of *Listeria* bacteria in a sample comprising:
    contacting the sample with a *Listeria* bacteria-specific ligand non-covalently immobilized on a glass substrate, wherein *Listeria* bacteria present in the sample binds to the ligand, wherein the bacteria-specific ligand is Leucocin A (LeuA);
    contacting the bound *Listeria* bacteria with a detection agent, wherein the detection agent binds to the *Listeria* bacteria in the sample; and
    detecting the presence of *Listeria* bacteria in the sample by measuring the quantity of detection agent bound to *Listeria* bacteria in the sample.

2. The assay according to claim 1, wherein the bacteria is *Listeria monocytogenes*.

3. The assay according to claim 1, wherein the detection agent is a gold nanocluster.

4. The assay according to claim 1, wherein the detection comprises fluorescence detection.

5. The assay according to claim 4, wherein if the fluorescent intensity of the detection agent for the sample is greater than the fluorescent intensity of a control, there are bacteria present in the sample.

6. An assay for determining the presence of *Listeria* bacteria in a sample comprising:
    contacting the sample with a *Listeria* bacteria-specific ligand immobilized on a polyvinylidene difluoride (PVDF) membrane, wherein *Listeria* bacteria present in the sample binds to the ligand, wherein the bacteria-specific ligand is Leucocin A (LeuA);
    contacting the bound *Listeria* bacteria with a detection agent, wherein the detection agent binds to the *Listeria* bacteria in the sample; and
    detecting the presence of *Listeria* bacteria in the sample by measuring the quantity of detection agent bound to *Listeria* bacteria in the sample.

7. The assay according to claim 6, wherein the bacteria is *Listeria monocytogenes*.

8. The assay according to claim 6, wherein the detection agent is a gold nanocluster.

9. The assay according to claim 6, wherein the detection comprises fluorescence detection.

10. The assay according to claim 9, wherein if the fluorescent intensity of the detection agent for the sample is greater than the fluorescent intensity of a control, there are bacteria present in the sample.

* * * * *